US006294574B1

(12) United States Patent
Cai et al.

(10) Patent No.: US 6,294,574 B1
(45) Date of Patent: Sep. 25, 2001

(54) COMPOUNDS AND METHODS FOR THE TREATMENT OF INFLAMMATORY AND IMMUNE DISORDERS

(75) Inventors: Xiong Cai, Allston; Sajjat Hussoin, Cambridge; San-Bao Hwang, Wayland; David Killian, Cambridge, all of MA (US); T. Y. Shen, Charlottesville, VA (US)

(73) Assignee: Cytomed, Inc., Cambridge, MA (US)

( * ) Notice: Subject to any disclaimer, the term of this patent is extended or adjusted under 35 U.S.C. 154(b) by 0 days.

(21) Appl. No.: 08/469,073

(22) Filed: Jun. 6, 1995

Related U.S. Application Data

(60) Division of application No. 08/062,391, filed on May 12, 1993, which is a continuation-in-part of application No. 07/933,991, filed on Aug. 24, 1992, now Pat. No. 5,434,151, which is a division of application No. 07/912,788, filed on Jul. 13, 1992, now Pat. No. 5,398,938.

(51) Int. Cl.$^7$ .................................................. A01N 43/08
(52) U.S. Cl. .......................................... 514/473; 549/476
(58) Field of Search ........................... 544/174, 176, 544/180; 546/256, 283, 284; 549/67, 70, 71, 72, 73, 74, 75, 78, 79, 80, 473, 478, 476, 477, 480, 483, 484, 487, 488, 491, 492, 494, 495, 496, 497, 498, 499, 500, 501, 502; 514/231.5, 237.2, 333, 337, 438, 445, 448, 471, 472, 473, 340, 913

(56) References Cited

U.S. PATENT DOCUMENTS

| | | | |
|---|---|---|---|
| 2,690,988 | 10/1954 | Jones et al. | 167/33 |
| 4,166,452 | 9/1979 | Generales, Jr. | 128/741 |
| 4,256,108 | 3/1981 | Theeuwes | 128/260 |
| 4,265,874 | 5/1981 | Bonsen et al. | 424/15 |
| 4,522,811 | 6/1985 | Eppstein et al. | 514/2 |
| 4,539,332 | 9/1985 | Biftu et al. | 514/461 |
| 4,595,693 | 6/1986 | Biftu et al. | 514/461 |
| 4,604,407 | 8/1986 | Haslanger et al. | 514/575 |
| 4,656,190 | 4/1987 | Shen et al. | 514/529 |
| 4,757,084 | 7/1988 | Biftu et al. | 514/438 |
| 4,841,968 | 6/1989 | Dunn et al. | 128/335.5 |
| 4,845,129 | 7/1989 | Anderson et al. | 514/600 |
| 4,871,756 | 10/1989 | Gillard et al. | 514/381 |
| 4,873,259 | 10/1989 | Summers, Jr. et al. | 514/443 |
| 4,876,346 | 10/1989 | Musser et al. | 546/172 |
| 4,891,363 | 1/1990 | Nakamura et al. | 514/94 |
| 4,910,206 | 3/1990 | Houlihan | 514/292 |
| 4,916,145 | 4/1990 | Tilley et al. | 514/357 |
| 4,959,361 | 9/1990 | Walser | 514/220 |
| 4,987,132 | 1/1991 | Mase et al. | 514/252 |
| 4,992,428 | 2/1991 | Houlihan et al. | 514/63 |
| 4,996,203 | 2/1991 | Biftu et al. | 514/231.5 |
| 5,001,123 | 3/1991 | Biftu et al. | 514/235.2 |
| 5,037,853 | 8/1991 | Brooks et al. | 514/595 |
| 5,047,420 | 9/1991 | Graham et al. | 514/484 |
| 5,110,831 | 5/1992 | Magolda et al. | 514/645 |
| 5,112,848 | 5/1992 | Brooks et al. | 514/424 |
| 5,169,854 | 12/1992 | Brooks et al. | 514/314 |
| 5,175,183 | 12/1992 | Brooks et al. | 514/438 |
| 5,183,818 | 2/1993 | Brooks et al. | 514/231.5 |
| 5,187,192 | 2/1993 | Brooks et al. | 514/445 |
| 5,234,950 | 8/1993 | Edwards et al. | 514/473 |
| 5,244,896 | 9/1993 | Borcherding et al. | 514/258 |
| 5,288,751 | 2/1994 | Brooks et al. | 514/438 |
| 5,326,787 | 7/1994 | Brooks et al. | 514/507 |
| 5,334,616 | 8/1994 | Brooks et al. | 514/438 |
| 5,344,843 | 9/1994 | Guthrie et al. | 514/473 |
| 5,358,938 | 10/1994 | Cai et al. | 514/231.5 |
| 5,420,164 | 5/1995 | Mishina et al. | 514/596 |
| 5,434,151 | 7/1995 | Cai et al. | 514/231.5 |
| 5,463,083 | 10/1995 | Biftu et al. | 549/71 |

FOREIGN PATENT DOCUMENTS

| | | | |
|---|---|---|---|
| 3701344 | 7/1987 | (DE) | C07D/495/14 |
| 3724031 | 1/1988 | (DE) | C07D/495/14 |
| 3724164 | 1/1988 | (DE) | C07D/487/04 |
| 2197650 | 5/1988 | (DE) | C07D/307/10 |
| 3936828 | 5/1990 | (DE) | C07D/495/14 |
| 4006471 | 9/1990 | (DE) | C07D/495/14 |
| 2233974 | 1/1991 | (DE) | C07D/401/12 |
| 0 144 804 | 6/1985 | (EP) | C07D/307/12 |
| 0 199 324 | 10/1986 | (EP) | C07D/307/10 |
| 0 217 204 | 4/1987 | (EP) | C07D/333/16 |
| 0 252 823 A1 | 1/1988 | (EP) | C07D/513/04 |
| 0 257 921 | 3/1988 | (EP) . | |
| 0 319 947 A2 | 6/1989 | (EP) | C07C/149/36 |

(List continued on next page.)

OTHER PUBLICATIONS

Backvall, et al., "A Stereocontrolled Organopalladium Route to 2,5–Disubstituted Pyrrolidine Derivatives. Application to the Synthesis of a Venom Alkaloid of the Ant Species *Monomorium latinode*," *J. Org. Chem*, 55:826–831 (1990).

(List continued on next page.)

Primary Examiner—John Kight
Assistant Examiner—Raymond Covington
(74) Attorney, Agent, or Firm—Kilpatrick & Cody

(57) ABSTRACT 2,5-Diaryl tetrahydrofurans, 2,5-diaryl tetrahydrothiophenes, 2,4-diaryl tetrahydrofurans, 2,4-diaryl tetrahydrothiophenes, 1,3-diaryl cyclopentanes, 2,4-diaryl pyrrolidines, and 2,5-diaryl pyrrolidines are disclosed that reduce the chemotaxis and respiratory burst leading to the formation of damaging oxygen radicals of polymorphonuclear leukocytes during an inflammatory or immune response. The compounds exhibit this biological activity by acting as PAF receptor antagonists, by inhibiting the enzyme 5-lipoxygenase, or by exhibiting dual activity, i. e., by acting as both a PAF receptor antagonist and inhibitor of 5-lipoxygenase.

A method to treat disorders mediated by PAF or leukotrienes is also disclosed, that includes administering an effective amount of one or more of the above-identified compounds or a pharmaceutically acceptable salt thereof, optionally in a pharmaceutically acceptable carrier.

10 Claims, 2 Drawing Sheets

FOREIGN PATENT DOCUMENTS

| | | | |
|---|---|---|---|
| 0 322 033 | 6/1989 | (EP) | C07D/307/12 |
| 0 338 993 A1 | 10/1989 | (EP) | C07D/495/14 |
| 0 365 089 A2 | 4/1990 | (EP) | C07D/333/18 |
| 0 367 110 A1 | 5/1990 | (EP) | C07D/495/22 |
| 0 388 309 A2 | 9/1990 | (EP) | C07D/513/04 |
| 0 402 150 A1 | 12/1990 | (EP) | C07D/307/12 |
| 0 402 151 | 12/1990 | (EP) | C07D/307/12 |
| 0 402 155 | 12/1990 | (EP) | C07D/405/04 |
| 0 402 156 | 12/1990 | (EP) | C07D/405/04 |
| 0 416 609 | 3/1991 | (EP) | C07D/333/58 |
| 0 617 032 | 9/1994 | (EP) | C07D/401/12 |
| 2 263 109 | 7/1993 | (GB) . | |
| WO 89/04299 | 5/1989 | (WO) . | |
| WO 90/12015 | 10/1990 | (WO) . | |
| WO 91/17157 | 11/1991 | (WO) . | |
| WO 92/09566 | 6/1992 | (WO) | C07C/273/18 |
| WO 92/13848 | 8/1992 | (WO) | C07D/307/14 |
| WO 92/15294 | 9/1992 | (WO) | A61K/31/34 |
| WO 93/01191 | 1/1993 | (WO) . | |
| WO 93/16075 | 8/1993 | (WO) . | |
| WO 94/01430 | 1/1994 | (WO) | C07D/333/18 |
| WO 94/04537 | 3/1994 | (WO) | C07D/495/04 |
| WO 94/06790 | 3/1994 | (WO) | C07D/339/06 |
| WO 95/18610 | 7/1995 | (WO) . | |
| WO 96/00212 | 1/1996 | (WO) . | |

OTHER PUBLICATIONS

Bartroli, J., et al., "Design of Potent Linear PAF Antagonists," *J. Med. Chem.*, 34:3328–3334 (1991).

Biftu, T., et al., *Abstr. of 6th Int. Conf. on Prostaglandins and Related Compounds*, Florence, Italy, p. 302 (Jun. 3–6, 1986).

Biftu, T., et al., "Confirmation and Activity of Tetrahydrofuran Lignans and Analogues as Specific Platelet Activating Factor Antagonists," *J. Med. Chem.*, 29(10):1917–1921 (1986).

Bowles, et al., A Convenient Preparation of Cyclic Ether Acetals Mediated by Trifluoroacetic Anhydride, *Synlett*, pp. 111–112 (1993).

Carlcellar, E., et al., "4–Substituted 2–Alkoxytetrahydrofurans as Potent and Long–Lasting PAF Antagonists," *J. Med. Chem.*, 35(4):676–683 (1992).

Carter, et al., "5–Lipoxygenase Inhibitory Activity of Zileuton," *J. of Pharmacol. and Exp. Thera.*, 256(3);929–937 (1991).

Corey, E.J. et al., "Dual Binding Modes to the Receptor for Platelet Activating Factor (PAF) of Anti–PAF Trans–2, 5–Diarylfurans," *Tetrahedron Letters*, 29(24):2899–2902 (1988).

Crawley, G.C., "Methoxytetrahydropyrans. A New Series of Selective and Orally Potent 5–Lipoxygenase Inhibitors," *J. Med. Chem.*, 35(14):2600–2609 (1992).

Danyoshi et al., "Pyrrolidine Derivatives as Inhibitors of Platelet Aggregation Induced by Platelet Activating Factor," *Chem. Pharm. Bull.*, 37(7):1969–1970 (1989).

Erez, et al., "Narcotic Antagonistic Potency of Bivalent Ligands Which Contain Beta–Naltrexamine. Evidence for Bridging between Proximal Recognition Sites," *J. of Med. Chem.*, 25(7):847–849 (1982).

Feinmark, S.J., "Leukotriene, $C_4$ Biosynthesis During Polymorphonuclear Leukocyte–Vascular Cell Interactions," *Methods in Enzymology*, Murphy and Fitzpatrick, eds., Academic Press, Inc., Harcourt Brace Jovanovich, publishers, New York, NY, vol. 187, pp. 559–560 (1990).

Foye, (Editor) "Bioisosterism," *Principles of Med. Chem.*, Second Edition, pp. 80–81 (Lea & Febiger, Philadelphia, 1981).

Goldstein, et al., "Dual Inhibitors of Platelet Activating Factor and 5–Lipoxygenase. I., 2,40Diaryl–1,3–dithiolanes," *Med. Chem. Res.*, 2:443–450 (1992).

Goldstein, et al., "Dual Inhibitors of Platelet Activating Factor and 5–Lipoxygenase. II. Novel 2,4–Diaryl–1,3–dithiolanes with Iron–Chelating Functionalities," *Med. Chem. Res.*, 2:451–456 (1992).

Graham, D.W., et al., "1,3–Diarylcyclopentanes: A New Class of Potent PAF Receptor Antagonists," 197th ACS National Meeting, Division of Medicinal Chemistry, poster No. 25, Dallas, Texas (Apr. 9–14, 1989).

Guthrie, R.W., et al., "Propenyl Carboxamide Derivatives As Antagonists of Platelet Activating Factor," *J. Med. Chem.*, 33:2856–2864 (1990).

Hwang, S., "Specific Receptors of Platelet–Activating Factor, Receptor Heterogeneity, and Signal Transduction Mechanisms," *J. Lipid Mediators*, 2:123–158 (1990).

Hwang, S., et al., "Trans–2, 5–bis–(3,4,5–trimethoxyphenyl)tetrahydrofuran," *Journal of Biological Chemistry*, 260(29):15639–15645 (1985).

Hwang, S., et al., "Biochemical and Pharmaceutical Charactgerization of L–659, 989: An Extremely Potent, Selective and Competitive Receptor Antagonist of Platelet–Activating Factor," *J. Pharmacol. Ther.*, 246(2):534–541 (1988).

Ikeda et al., "Preparation of Hydroxamic Acid and N–Hydroxyurea Derivatives and Their Use as Lipoxygenase Inhibitors," *Chemical Abstracts*, vol. 118, Abstract No. 59426 (1993).

Lavé, D., et al., "Pyrrolo [1,2–c]Thiazole Derivatives: Potent PAF Receptor Antagonists," *Drugs of the Future*, 14(9):891–898 (1989).

McColl, S.R., "Determination of 5–Lipoxygenase Activity in Human Polymorphonuclear Leukocytes Using High–Performance Liquid Chromatography," *J. Chromatography*, 378:444–449 (1986).

Musser, J.H., et al., "5–Lipoxygenase: Properties, Pharmacology, and the Quinolinyl(bridged)aryl Class of Inhibitors," *J. Med. Chem.*, 35(14):2502–2524 (1992).

O'Donnell, M., et al., "Comparison of the Pulmonary Pharmacoogy of Leukotrienes and PAF: Effects of Their Antagonists," *Therapeutic Approaches to Inflammatory Diseases*, Proceedings of the Fourth International Research Association, pp. 169–193; White Haven, Pennsylvania (Oct. 23–27, 1988).

Ogiso, A., et al., "The Structure of Futoenone, A Novel Spiro–Cyclohexadienone Derivative," *Tetrahedron Letters*, No. 16, pp. 2003–2008 (1968).

Ogiso, a., et al., "The Structure and Total Synthesis of Futoenone, a Constitute of *Piper futokadzura* SIEB. et Zucc.[1])," *Chem. Pharm. Bull.*, 18(1):105–114 (1970).

Page, C. et al., "PAF: New Antagonists, New Roles in Diseases and a Major Role in Reproductive Biology," *Trends in Pharmacol. Sci.*, pp. 256–257 (1989).

Ponpipom, M.M., et al., "Structure–Activity Relationships of Kadsurenone Analogues," *J. Med. Chem.*, 30:136–142 (1987).

Ponpipom, M.M., et al., "(±)–TRANS–2–(3–Methoxy–5–Methylsulfonyl–4–Propoxyphenyl)–5–(3,4,5–Trimethoxyphenyl) Tetrahydrofuran (L–659,989), A Novel, Potent PAF Receptor Antagonist," *Biochemical and Biophysical Research Communications*, 150(3):1213–1220 (1988).

Sahoo, et al., "Synthesis and Biological Activity of MK 287 (L–680,573): A Potent, Specific, and Orally Active PAF Receptor Antagonist," *Bioorg. & Med. Chem. Lett.*, 1(16):327–332 (1991).

Schwenk, et al., "Identification of 5–Oxo–15–hydroxy–6,8,11,13–eicosatetraenoic Acid as a Novel and Potent human Eosinophil Chemotactic Eicosanoid," *J. Biol. Chem.* 267(18):12482–12488 (1992).

Seminaro and Gleich, "The role of eosinophils in the pathogenesis of asthma," *Curr. Opin. in Immunol.*, 6:860–864 (1994).

Shen, T.Y., "Characterization of a Platelet–Activating Factor Receptor Antagonist Isolated from Haifenteng (*Piper futokadsura*): Specific Inhibition on in vitro and in vivo Platelet–Activating Factor–Induced Effects," *Proc. Nat'l. Acad. Sci. USA*, 82:672–676 (1985).

Shen, T.Y., et al., "The Chemical and Biological Properties of PAF Agonists, Antagonists, and Biosynthetic Inhibitors," *Platelet–Activating Factor and Related Lipid Mediators*, Plenum Press, New York, NY, pp. 153–190 (1987).

Shen and Hussaini, "Kadsurenone and Other Related Lignans as Antagonists of Platelet–Activating Factor Receptor," *Methods in Enzymol.*, 187:446–454 (1990).

Shizuri, et al., "Synthesis of some physiologically active substances using anodic oxidation of phenols as a key–step," *Tennen Yuki Kagobutsu Toronkai Koen Yoshishu, Chem. Abstracts*, Abstract 209491p (1983).

Talapatra, et al., "Maglifloenone,a novel spirocyclohexadienone neolignan and other constituents from *Magnolia liliflora*," *Chem. Abstracts*, Abstract No. 52493k (1982).

Terashita, et al., "CV–3988—A Specific Antagonist of Platelet Ativating Factor (PAF)," *Life Sciences*, 32(17):1975–1982 (1983).

Weber, K.H., et al., "Hetrazepines as Antagonists of Platelet Activating Factor," *Medicinal Research Reviews*, 9(1):181–218 (Jan.–Mar. 1989).

Wood, et al., "Cyclic Ether Acetal Platelet Activating Factor (PACF) Receptor Antagonists II: Imidazo[4,5–c]Pyridyl Derivatives," *Bioorg. & Med. Chem. Lett.*, 3(8):1499–1504 (1993).

Yeadon, et al., "Effect of BW B70C, a novel inhibitor of arachidonic acid 5–lipoxygenase, on allergen–induced bronchoconstriction and late–phase lung eosinophil accumulation in sensitised guinea–pigs," *Agents and Actions*, 38:8–18 (1993).

Communication dated Mar. 4, 1997 in European Patent Appl. No. 95907972.4.

COMPOUNDS AND METHODS FOR THE TREATMENT OF INFLAMMATORY AND IMMUNE DISORDERS

This application is a divisional of U.S. Ser. No. 08/062,391, filed on May 12, 1993, (now allowed), which is a continuation-in-part of U.S. Ser. No. 07/933,991, now U.S. Pat. No. 5,434,151, filed on Aug. 24, 1992, by Xiong Cai, Sajjat Hussoin, San Bao Hwang, David Killian, and T. Y. Shen, which is a divisional application of U.S. Ser. No. 07/912,788, now U.S. Pat. No. 5,358,938, filed Jul. 13, 1992, by Xiong Cai, Sajjat Hussoin, San Bao Hwang, David Killian, and T. Y. Shen.

BACKGROUND OF THE INVENTION

This invention is in the area of pharmaceutical compositions and methods for the treatment of inflammatory and immune disorders, and specifically provides novel compounds that reduce damage arising from an inflammatory or immune response. The compounds exhibit this biological activity by acting as PAF receptor antagonists, by inhibiting the enzyme 5-lipoxygenase, or by exhibiting dual activity, i.e., by acting as both a PAF receptor antagonist and inhibitor of 5-lipoxygenase.

Platelet activating factor (PAF, 1-O-alkyl-2-acetyl-sn-glycerol-3-phosphorylcholine) is a potent inflammatory phospholipid mediator with a wide variety of biological activities. PAF was initially identified as a water soluble compound released by immunoglobulin E (IgE)-sensitized rabbit basophils. It is now known that PAF is also generated and released by monocytes, macrophages, polymorphonuclear leukocytes (PMNs), eosinophils, neutrophils, natural killer lymphocytes, platelets and endothelial cells, as well as by renal and cardiac tissues under appropriate immunological and non-immunological stimulation. (Hwang, "Specific receptors of platelet-activating factor, receptor heterogeneity, and signal transduction mechanisms", *Journal of Lipid Mediators* 2, 123 (1990)). PAF causes the aggregation and degranulation of platelets at very low concentrations. The potency (active at $10^{-12}$ to $10^{-9}$M), tissue level (picomoles) and short plasma half life (2–4 minutes) of PAF are similar to those of other lipid mediators such as thromboxane $A_2$, prostaglandins, and leukotrienes. PAF mediates biological responses by binding to specific PAF receptors found in a wide variety of cells and tissues. Structure-activity studies on PAF and its analogs indicate that the ability of PAF to bind to these receptors is highly stricture specific and stereospecific. (Shen, et al., "The Chemical and Biological Properties of PAF Agonists, Antagonists, and Biosynthetic Inhibitors", *Platelet-Activating Factor and Related Lipid Mediators*, F. Snyder, Ed. Plenum Press, New York, N.Y. 153 (1987)).

While PAF mediates essential biological responses, it also appears to play a role in pathological immune and inflammatory responses. Many published studies have provided evidence for the involvement of PAF in human diseases, including arthritis, acute inflammation, asthma, endotoxic shock, pain, psoriasis, ophthalmic inflammation, ischemia, gastrointestinal ulceration, myocardial infarction, inflammatory bowel diseases, and acute respiratory distress syndrome. Animal models also demonstrate that PAF is produced or increased in certain pathological states.

The involvement of PAF in pathological inflammatory and immune states has stimulated a substantial research effort to identify PAF receptor antagonists. In 1983, a phospholipid analog referred to as CV-3988 (rac-3-(N-n-octadecylcarbamoyloxy-w-methoxypropy)-2-thiazolioethyl phosphate) was reported to have PAF receptor antagonist properties. (Terashita, et al., *Life Sciences* 32, 1975 (1983)). In other early work in this area, Shen, et al., (in *Proc. Natl. Acad. Sci. USA* 82, 672 (1985)), reported that kadsurenone, a neolignan derivative isolated from Piper futokadsura Sieb et Zucc (a Chinese herbal plant) was a potent, specific and competitive inhibitor of PAF activity at the receptor level. Hwang, et al., disclosed in 1985 that trans-2,5-bis-(3,4,5-trimethoxyphenyl)tetrahydrofuran (L-652,731) inhibits the binding of tritiated PAF to PAF receptor sites. (Hwang, et al., "Trans-2,5-bis-(3,4,5-trimethoxyphenyl)tetrahydrofuran", *Journal of Biological Chemistry* 260, 15639 (1985).) L-652,731 was found to be orally active, and to inhibit PAF-induced rat cutaneous vascular permeability at a dosage of 30 mg/kg body weight. The compound was found to have no effect on the enzyme 5-lipoxygenase. Hwang, et al., also reported that trans-L-652,731, wherein the aryl groups at the 2 and 5 positions are on opposite sides of the plane of the tetrahydrofuran ring, is approximately 1000 times more potent than cis-L-652,731, wherein the 2 and 5 aryl substituents are on the same side of the plane of the tetrahydrofuran ring.

In 1988, Hwang, et al., reported that L-659,989 (trans-2-(3-methoxy-4-propoxyphenyl-5-methylsulfonyl)-5-(3,4,5-trimethoxyphenyl)tetrahydrofuran) is an orally active, potent, competitive PAF receptor antagonist, with an equilibrium inhibition constant 10 times greater than that of trans-L-652,731. (Hwang, et al., *J. Pharmacol. Exp. Ther.* 246, 534 (1988).)

U.S. Pat. Nos 4,996,203, 5,001,123 and 4,539,332 to Biftu, et al. and European Patent Application Nos. 89202593.3, 90306235.4, and 90306234.7 disclose that a specific class of 2,5-diaryl tetrahydrofurans are PAF receptor antagonists.

Leukotrienes, like PAF, are potent local mediators, playing a major role in inflammatory and allergic responses, including arthritis, asthma, psoriasis, and thrombotic disease. Leukotrienes are straight chain eicosanoids produced by the oxidation of arachidonic acid by lipoxygenases. Arachidonic acid is oxidized by 5-lipoxygenase to the hydroperoxide 5-hydroperoxyeicosatetraenoic acid (5-HPETE), which is converted to leukotriene $A_4$, which in turn can be converted to leukotriene $B_4$, $C_4$, or $D_4$. The slow-reacting substance of anaphylaxis is now known to be a mixture of leukotrienes $C_4$, $D_4$, and $E_4$, all of which are potent bronchoconstrictors.

There has been a research effort to develop specific receptor antagonists or inhibitors of leukotriene biosynthesis, to prevent or minimize pathogenic inflammatory responses mediated by these compounds.

Leukotrienes are released simultaneously from leukocytes with PAF, possibly from a common phospholipid precursor such as 1-O-hexadecyl-2-arachidonyl-sn-glycerophosphocholine, and upon cellular activation, act synergistically with PAF in many biological models. Recently, it was reported that the tetrahydrothiophene derivative of L-652,731, trans-2,5-bis-(3,4,5-trimethoxyphenyl) tetrahydrothiophene (L-653,150), is a potent PAF antagonist and a moderate inhibitor of 5-lipoxygenase. It has been disclosed that certain 2,5-diaryl tetrahydrothiophenes are PAF antagonists and leukotriene synthesis inhibitors. (Biftu, et al., *Abstr. of 6th Int. Conf. on Prostaglandins and Related Compounds*, Jun. 3–6, 1986, Florence, Italy; U.S. Pat. No. 4,757,084 to Biftu). European Patent Application Nos. 90117171.0 and 901170171.0 disclose indole, benzofuran, and benzothiophene lipoxygenase inhibiting compounds. Given the significant number of pathological immune and inflammatory responses that are mediated by PAF and leukotrienes, there remains a need to identify new compounds and compositions that exhibit PAF receptor antagonistic activity or inhibit the enzyme 5-lipoxygenase.

Therefore, it is an object of the present invention to provide compounds that reduce the chemotaxis and respiratory burst leading to the formation of damaging oxygen radicals during an inflammatory or immune response.

It is another object of the present invention to provide pharmaceutical compositions or the treatment of pathological immune or inflammatory disorders mediated by PAF or products of 5-lipoxygenase.

It is another object of the present invention to provide methods for the treatment of pathological immune or inflammatory disorders mediated by PAF or products of 5-lipoxygenase.

SUMMARY OF THE INVENTION 2,5-Diaryl tetrahydrothiophenes, tetrahydrofurans, and pyrrolidines, 1,3-diaryl cyclopentanes, and 2,4-diaryl tetrahydrothiophenes, tetrahydrofurans and pyrrolidines for the treatment of pathological immune or inflammatory disorders are disclosed of the structures:

Formula I wherein:

$Ar^1 =$ or $Ar^2 =$ or wherein:

X is O, S, S(O), S(O)$_2$, CR$^9$, or NR$^{10}$;

W is independently:
(1) —AN(OM)C(O)N(R$^3$)R$^4$, —AN(R$^3$)C(O)N(OM)R$^4$, —AN(OM)C(O)R$^4$, —AC(O)N(OM)R$^4$, —N(OM)C(O)N(R$^3$)R$^4$, —N(R$^3$)C(O)N(OM)R$^4$, —N(OM)C(O)R$^4$, —C(O)N(OM)R$^4$, —OR$^6$N(R$^5$)R$^6$—(C$_5$H$_4$N)R$^6$R$^7$, —OR$^6$N(COR$^5$)R$^6$—(C$_5$H$_4$N)R$^6$R$^7$, —OR$^6$OC(O)N(COR$^5$)R$^6$—(C$_5$H$_4$N)R$^6$R$^7$, —OR$^6$O(CO)N(CO$_2$R$^6$)R$^6$(C$_5$H$_4$N)R$^6$R$^7$, —A(C$_5$H$_4$N)R$^6$R$^7$, or —OR$^6$N(CO$_2$R$^5$)R$^6$—(C$_5$H$_4$N)R$^6$R$^7$;

(2) an amidohydroxyurea of the formula: —N(R$^{19}$)C(O)C(R$^{19}$)$_2$N(OM)C(O)NHR$^{20}$, —C(O)N(R$^{19}$)C(R$^{19}$)$_2$N(OM)C(O)NHR$^{20}$, —AN(R$^{19}$)C(O)C(R$^{19}$)$_2$N(OM)C(O)NHR$^{20}$, —AC(O)N(R$^{19}$)C(R$^{19}$)$_2$N(OM)C(O)NHR$^{20}$, —NHC(O)N(OM)C(R$^{19}$)$_2$C(O)N(R$^{19}$)$_2$; or —NHC(O)N(OM)C(R$^{19}$)$_2$N(R$^{19}$)C(O)R$^{19}$;

(3) an oxalkane of the structure:

wherein n and m are independently 1–4;

(4) a thioalkane of the structure:

or (5) a quinolylmethoxy of the structure:

n is 1 or 2;

m is 1, 2 or 3;

p is 0 or 1;

A is alkyl, alkenyl, alkynyl, alkaryl, aralkyl, halo lower alkyl, halo lower alkenyl, halo lower alkynyl, —C$_{1-10}$alkyl(oxy)C$_{1-10}$alkyl, —C$_{1-10}$alkyl(thio)C$_{1-10}$-alkyl, —N(R$^3$)C(O)alkyl, —N(R$^3$)C(O)alkenyl, —N(R$^3$)C(O)alkynyl, —N(R$^3$)C(O)(alkyl)oxy(alkyl), —N(R$^3$)C(O)(alkyl)thio(alkyl), —N(R$^3$)C(O)N(alkyl), —N(R$^3$)C(O)N(alkenyl), —N(R$^3$)C(O)N(alkynyl), —N(R$^3$)C(O)N(alkyl)oxy(alkyl), —N(R$^3$)C(O)N(alkyl)thio(alkyl), —N(R$^3$)C(O$_2$)alkyl, —N(R$^3$)C(O$_2$)alkenyl, —N(R$^3$)C(O$_2$)alkynyl, —N(R$^3$)C(O$^2$)(alkyl)oxy(alkyl), —N(R$^3$)C(O$_2$)(alkyl)thio(alkyl), —OC(O$_2$)alkyl, —OC(O$_2$)alkenyl, —OC(O$_2$)alkynyl, —OC(O$_2$)(alkyl)oxy(alkyl), —OC(O$_2$)(alkyl)thio(alkyl), —N(R$^3$)C(S)alkyl, —N(R$^3$)C(S)alkenyl, —N(R$^3$)C(S)alkynyl, —N(R$^3$)C(S)(alkyl)oxy(alkyl), —N(R$^3$)C(S)(alkyl)thio(alkyl), —N(R$^3$)C(S)N(alkyl), —N(R$^3$)C(S)N(alkenyl), —N(R$^3$)C(S)N(alkynyl), —N(R$^3$)C(S)N(alkyl)oxy(alkyl), —N(R$^3$)C(S)N(alkyl)thio(alkyl), —N(R$^3$)C(S)S(alkyl), —N(R$^3$)C(S)S(alkenyl), —N(R$^3$)C(S)S(alkynyl), —N(R$^3$)C(S)S(alkyl)oxy(alkyl), —N(R$^3$)C(S)S(alkyl)thio(alkyl), —SC(S)S(alkyl), —SC(S)S(alkenyl), —SC(S)S(alkynyl), —SC(S)S(alkyl)oxy(alkyl), and —SC(S)S(alkyl)thio(alkyl);

M is hydrogen, a pharmaceutically acceptable cation, or a metabolically cleavable leaving group;

Y is independently:

(a) hydrogen;

(b) R$^{1-6}$, R$^8$, R$^{10}$, —OR$^3$, —OR$^{11}$, —OR$^{12}$, R$^3$S—, R$^5$S—, R$^3$SO—, R$^5$SO—, R$^3$SO$_2$—, R$^5$SO$_2$—, CF$_3$O—, CF$_3$S—, CF$_3$SO—, —CF$_3$SO$_2$, —OCH$_2$oxycyclopropyl, —OCH$_2$C(O)OR$^3$, —OCH₂OR³, —OCH₂C(O)R³, —OCH₂C₃₋ₛcycloalkyl, —OCH₂CH(R³)R³, —OCH₂cyclopropyl, —OCH₂-aryl, —OCH₂CH(OH)CH₂OH, aryl-CH₂—SO₂—, (R³)₂CHCH₂SO₂—, —CH₂CH(OH)CH₂OH, CF₃SO₂—, R³R⁴N—, —OCH₂CO₂R³, —NR³COR³, —OCONH₂, —OCONR³R⁴, —CONH₂, —CONR³R⁴, —CR³R³R⁴, —SO₂NR³R⁴, —SONR³R⁴, —CH₃OCH₂NR³R⁶, —SNR³R⁴, —CO₂R³, —NR³R⁴SO₂R³, —NR³R⁴SOR³, —COR³, —CONR³, —NO₂, —CN, —N(R⁵)CONR³R⁴, —CH₂N(R⁵)CONR³R⁴, —R⁶NR³R⁴, —OR⁶NR³R⁴, —O(O)CR⁵, —O(O)CNR³R⁴,

—SR⁶NR³R⁴, —S(O)R⁶NR³R⁴, —SO₂R⁶NR³R⁴,

—SR⁶OH, —S(O)R⁶OH, —SO₂R⁶OH, —OR⁶OC(O)N(CO₂R⁶)R⁶; O-alkyl-N-(aryl)-C(O)-heterocycle;

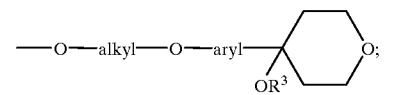

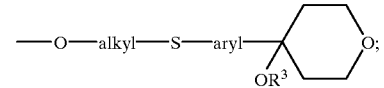

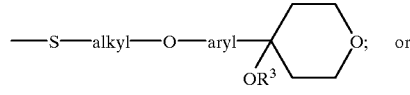

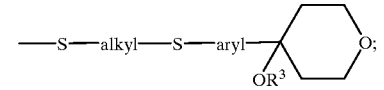

(c) a heterocycle, including but not limited to, pyrryl, furyl, pyridyl; 1,2,4-thiadiazolyl; pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbazolyl, benzimidazolyl, and isoxazolyl, optionally substituted with a group described in Y section (b);

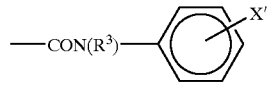

wherein X' is halo such as F, Cl, Br and I; —C(O)aryl; CF₃; OR³; —NR₃COR³; —OC(O)NH₂; —CR³R³R⁴; —C(O)R³; —CH₂OR³; —CH₂CO₂R³; —CH₂OC(O)R³; R³CH(R³)CH₂SO₃; —NHCH₂COOR³; N+R³R³R⁴R⁷; —NR³SO₂R³; COR³; NO₂; or CN; or

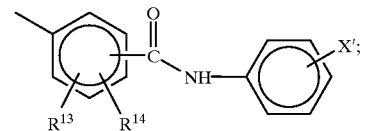

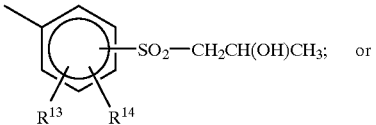

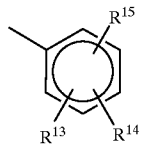

wherein R¹³, R¹⁴ and R¹⁵ independently represents: BO— wherein B is —CH₂-oxacyclopropyl, —CH₂OR³, —CH₂C(O)R³, —CH₂CH(R³)R³, —CH₂Aryl, —CH₂CH(OH)—CH₂OH; R³C(R³)₂CH₂SO₂; or R¹³–R¹⁴ or R¹⁴–R¹⁵ are joined together to form a bridge such as —OCHR²CHR²—S(O)ₙ wherein n is 0 to 3; or

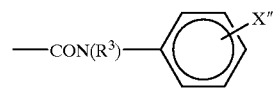

where X' is halo, —C(O)aryl, —CF₃, or —OR³; —CH₂OR³; —CH₂CO₂R³; —CH₂C(O)R³; —NHCH₂COOR³; or —N+R³R³R⁴R⁷

R¹ and R² are independently hydrogen, or lower alkyl, specifically including lower alkyl of 1–6 carbon atoms, e.g., methyl, cyclopropylmethyl, ethyl, isopropyl, butyl, pentyl and hexyl, as well as C₃₋₈ cycloalkyl, for example, cyclopentyl; halo lower alkyl, especially C₁₋₆ haloalkyl, for example, trifluoromethyl; halo, especially fluoro; —COOH; —CONR¹⁶R¹⁷ wherein R¹⁶ and R¹⁷ independently represent C₁₋₆ alkyl and hydrogen, —COOR³, lower alkenyl, especially C₂₋₆ alkenyl, e.g., vinyl, allyl, CH₃CH=CH—CH₂—CH₂, and CH₃CH₂)₃—CH=CH—; —C(O)R³; —CH₂OR³; lower alkynyl, especially C₂₋₆ alkynyl, e.g., —C≡CH; —CH₂NR³R⁴; —CH₂SR³; =O; —OR³; or —NR³R⁴;

R³ and R⁴ are independently alkyl, alkenyl, alkynyl, aryl, aralkyl, alkaryl, hydrogen, C₁₋₆ alkoxy-C₁₋₁₀ alkyl, C₁₋₆ alkylthio-C₁₋₁₀ alkyl, and C₁₋₁₀ substituted alkyl (wherein the substituent is independently hydroxy or carbonyl, located on any of C₁₋₁₀);

R⁵ is lower alkyl, lower alkenyl, lower alkynyl, hydroxyl, hydrogen, halo lower alkyl, halo lower alkenyl, halo lower alkynyl, aralkyl, or aryl;

R⁶ is lower alkyl, lower alkenyl, lower alkynyl, aralkyl, halo lower alkyl, halo lower alkenyl, halo lower alkynyl, or aryl;

R⁷ is an organic or inorganic anion;

R⁸ is halo alkyl, halo lower alkyl, halo lower alkenyl, halo lower alkynyl, lower alkenyl, lower alkynyl, aralkyl, or aryl;

R⁹ is independently hydrogen, halogen, lower alkyl, halo lower alkyl, lower alkenyl, lower alkynyl, —CONR³R⁴, —C(O)R⁵, —CO₂R⁵, —CH₂OR⁵, —CH$_2$NR$^5$R$^5$, —CH$_2$SR$^5$, =O, =NR$^5$, —NR$^3$R$^4$, —NR$^3$R$^4$R$^7$, or —OR$^5$;

R$^{10}$ is —R$^3$, —R$^8$, —C(O)N(OR$^3$)R$^3$, or —OR$^3$.

R$^{11}$ is phenyl-S(O)$_g$-lower alkyl-; (R$^3$O)$_d$-phenyl-S(O)$_g$-lower alkyl-; (R$^3$R$^3$N)$_d$phenyl-S(O)$_g$-lower alkyl-; (CN)$_d$-phenyl-S(O)$_g$-lower alkyl-; (halo)$_d$-phenyl-S(O)$_g$-lower alkyl-; (R$^3$COO)$_d$-phenyl-S(O)$_g$-lower alkyl-; (R$^3$OCO)$_d$-phenyl-S(O)$_g$-lower alkyl-; (R$^3$CO)$_d$- phenyl-S(O)$_g$-lower alkyl-; phenyl-O-lower alkyl-; (R$^3$O)$_d$-phenyl-O-lower alkyl-; (CN)$_d$-phenyl-O-lower alkyl-; (halo)$_d$-phenyl-O-lower alkyl-; (R$^3$COO)$_d$-phenyl-O-lower alkyl-; (R$^3$OCO)$_d$-phenyl-O-lower alkyl-; or (R$^3$CO)$_d$-phenyl-O-lower alkyl- where d is 1, 2, 3, 4 or 5; and g is 0, 1, or 2.

R$^{12}$ is alkyl; substituted alkyl wherein the substituent is selected from the group consisting of hydroxy and amino; -lower alkyl-O-R$^{18}$, wherein R$^{18}$ is —PO$_2$(OH)—M+ or —PO$_3$(M+)$_2$, wherein M+ is a pharmaceutically acceptable cation; —C(O)(CH$_2$)$_2$CO$_2$—M+, or —SO$_3$—M+; -lower alkylcarbonyl-lower alkyl; -carboxy lower alkyl; -lower alkylarnino-lower alkyl; N,N-di-substituted amino lower alkyl-, wherein the substituents each independently represent lower alkyl; pyridyl-lower alkyl; imidazolyl-lower alkyl; imidazolyl-Y-lower alkyl wherein Y is thio or amino; morpholinyl-lower alkyl; pyrrolidinyl-lower alkyl; thiazolinyl-lower alkyl; piperidinyl-lower alkyl; morpholinyl-lower hydroxyalkyl; N-pyrryl; piperazinyl-lower alkyl; N-substituted piperazinyl-lower alkyl, wherein the substituent is lower alkyl; triazolyl-lower alkyl; tetrazolyl-lower alkyl; tetrazolylamino-lower alkyl; or thiazolyl-lower alkyl;

R$^{19}$ is H, lower alkyl, or lower alkenyl; and

R$^{20}$ is H, halogen, lower alkoxy, or lower alkyl;

Formula II

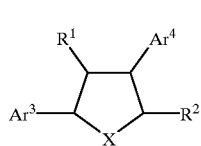

Ar$^3$ and Ar$^4$ are independently

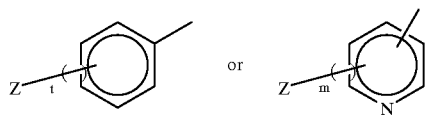

wherein:

X is O, S, S(O), S(O)$_2$, or NR$^{10}$;

m is 1, 2, or 3;

t is 1, 2, 3, or 4;

Z is independently W or Y; and

Formula III

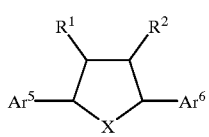

wherein Ar$^5$ is:

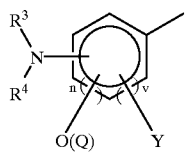

wherein Ar$^6$ is:

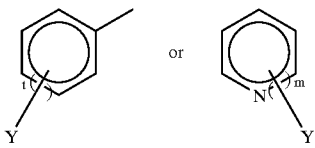

v is 0, 1, or 2; and

Q is selected from the group consisting of substituted C$_1$ to C$_{12}$ alkyl wherein the substituent is selected from the group consisting of hydroxy and amino, alkylcarbonylalkyl, alkyl; lower alkyl S(O)$_m$-lower alkyl in which m is 1 or 2; imidazolyl lower alkyl, morpholinyl lower alkyl, thiazolinyl lower alkyl, piperidinyl lower alkyl, imidazolylcarbonyl, morpholinyl carbonyl, amorpholinyl (lower alkyl) aminocarbonyl, N-pyrrylpyridinyl-lower alkyl; pyridylthio-lower alkyl; morpholinyl-lower alkyl; hydroxyphenylthio-lower alkyl; cyanophenylthio-lower alkyl; imidazolylthio-lower alkyl; triazolylthio-lower alkyl; triazolylphenylthio-lower alkyl; tetrazolylthio-lower alkyl; tetrazolylphenylthio-lower alkyl; aminophenylthio-lower alkyl; N,N-di-substituted aminophenylthio-lower alkyl wherein the amine substituents each independently represent lower alkyl; amidinophenylthio-lower alkyl; phenylsulfinyl-lower alkyl; or phenylsulfonyl lower alkyl; -lower alkyl-O-R$^{18}$, wherein R$^{18}$ is —PO$_2$(OH)—M+ or —PO$_3$(M+)$_2$, wherein M+ is a pharmaceutically acceptable cation; —C(O)(CH$_2$)$_2$CO$_2$—M+, or —SO$_3$—M+; -lower alkylcarbonyl-lower alkyl; -carboxy lower alkyl; -lower alkylamino-lower alkyl; N,N-di-substituted amino lower alkyl, wherein the amine substituents each independently represent lower alkyl; pyridyl-lower alkyl; imidazolyl-lower alkyl; imidazolyl-Y-lower alkyl wherein Y is thio or amino; morpholinyl-lower alkyl; pyrrolidinyl-lower alkyl; thiazolinyl-lower alkyl; piperidinyl-lower alkyl; morpholinyl-lower hydroxyalkyl; N-pyrryl; piperazinyl-lower alkyl; N-substituted piperazinyl-lower alkyl, wherein the amine substituent is lower alkyl; triazolyl-lower alkyl; tetrazolyl-lower alkyl; tetrazolylamino-lower alkyl; or thiazolyl-lower alkyl.

These compounds in general reduce the chemotaxis and respiratory burst leading to the formation of damaging oxygen radicals of polymorphonuclear leukocytes during an inflammatory or immune response. The compounds exhibit this biological activity by acting as PAF receptor antagonists, by inhibiting the enzyme 5-lipoxygenase, or by exhibiting dual activity, i. e., by acting as both a PAF receptor antagonist and inhibitor of 5-lipoxygenase.

A method to treat disorders mediated by PAF or leukotrienes is also disclosed, that includes administering an effective amount of one or more of the above-identified compounds or a pharmaceutically acceptable salt thereof, optionally in a pharmaceutically acceptable carrier, to reduce formation of oxygen radicals.

The compounds disclosed herein can also be used as research tools to study the structure and location of PAF receptors as well as biological pathways involving leukotrienes.

DETAILED DESCRIPTION OF THE INVENTION

Figure 1A:
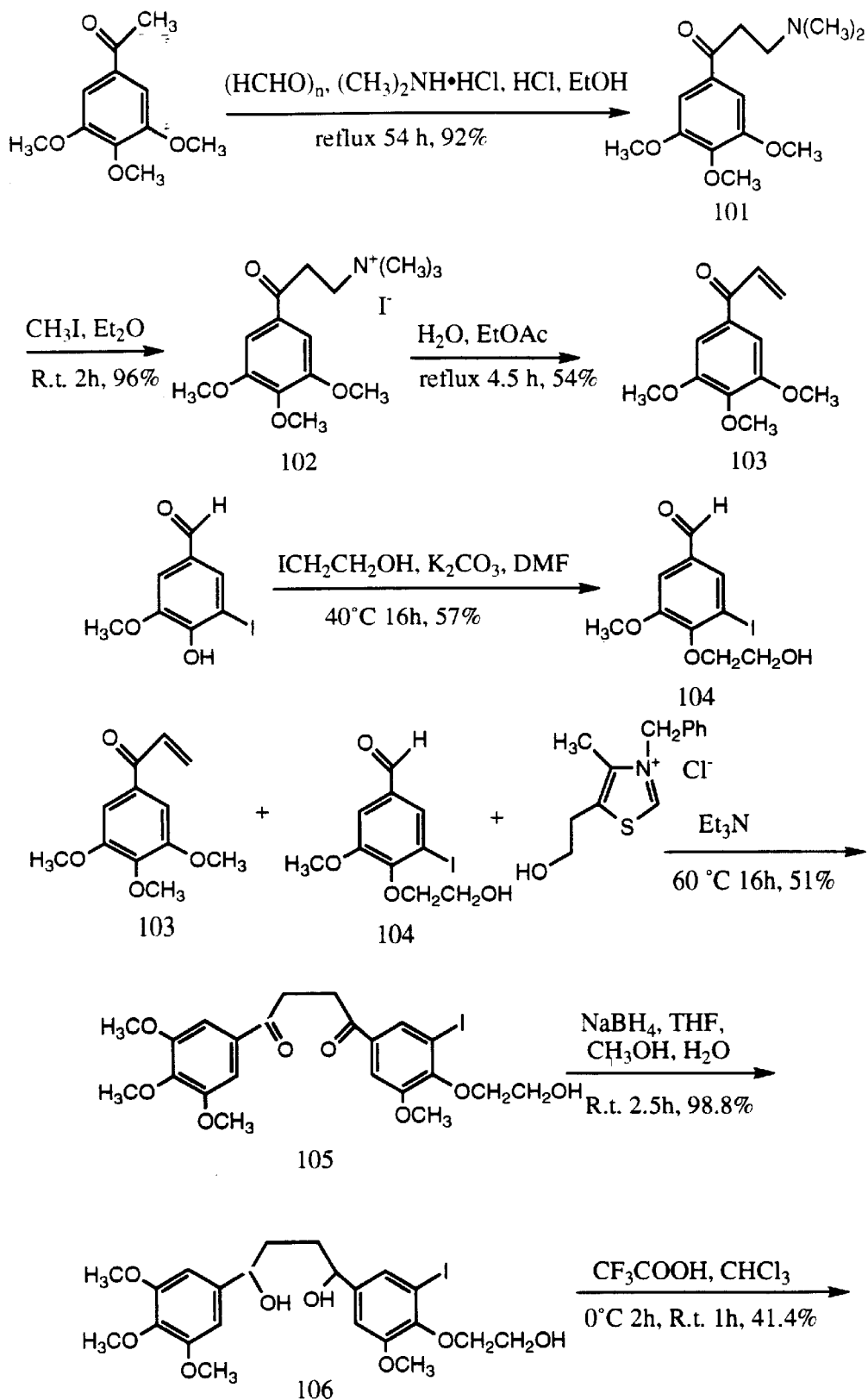
FIGS. 1a and 1b provide a schematic illustration of a process for the preparation of trans-2-[5-(N'-methyl-N'-hydroxyureidylmethyl)-3-methoxy-4-p-chlorophenylthioethoxyphenyl]-5-(3,4,5-trimethoxyphenyl) tetrahydrofuran.

I. Description and Synthesis of the Compounds

A. Compounds

The term alkyl, as used herein, unless otherwise specified, refers to a saturated straight, branched, or cyclic hydrocarbon of $C_1$ to $C_{10}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

The term lower alkyl, as used herein, and unless otherwise specified, refers to a $C_1$ to $C_6$ saturated straight, branched, or cyclic (in the case of $C_{5-6}$) hydrocarbon, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

The term alkenyl, as referred to herein, and unless otherwise specified, refers to a straight, branched, or cyclic (in the case of $C_{5-6}$) hydrocarbon of $C_2$ to $C_{10}$ with at least one double bond.

The term lower alkenyl, as referred to herein, and unless otherwise specified, refers to an alkenyl group of $C_2$ to $C_6$, and specifically includes vinyl and allyl.

The term lower alkylamino refers to an amino group that has one or two lower alkyl substituents.

The term alkynyl, as referred to herein, and unless otherwise specified, refers to a $C_2$ to $C_{10}$ straight or branched hydrocarbon with at least one triple bond.

The term lower alkynyl, as referred to herein, and unless otherwise specified, refers to a $C_2$ to $C_6$ alkynyl group, specifically including acetylenyl and propynyl.

The term aryl, as used herein, and unless otherwise specified, refers to phenyl or substituted phenyl, wherein the substituent is halo or lower alkyl.

The term halo, as used herein, includes fluoro, chloro, bromo, and iodo.

The term halo (alkyl, alkenyl, or alkynyl) refers to a (alkyl, alkenyl, or alkynyl) group in which at least one of the hydrogens in the group has been replaced with a halogen atom.

The term heterocycle or heteroaromatic, as used herein, refers to an aromatic moiety that includes at least one sulfur, oxygen, or nitrogen in the aromatic ring. Non-limiting examples are pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbazolyl, benzimidazolyl, and isoxazolyl.

The term aralkyl refers to an aryl group with an alkyl substituent.

The term alkaryl refers to an alkyl group that has an aryl substituent.

The term organic or inorganic anion refers to an organic or inorganic moiety that carries a negative charge and can be used as the negative portion of a salt.

The term "pharmaceutically acceptable cation" refers to an organic or inorganic moiety that carries a positive charge and that can be administered in association with a pharmaceutical agent, for example, as a countercation in a salt. Pharmaceutically acceptable cations are known to those of skill in the art, and include but are not limited to sodium, potassium, and quaternary amine.

The term "metabolically cleavable leaving group" refers to a moiety that can be cleaved in vivo from the molecule to which it is attached, and includes but is not limited to an organic or inorganic anion, a pharmaceutically acceptable cation, acyl (for example (alkyl)C(O), including acetyl, propionyl, and butyryl), alkyl, phosphate, sulfate and sulfonate.

The term "enantiomerically enriched composition or compound" refers to a composition or compound that includes at least 95% by weight of a single enantiomer of the compound.

The term PAF receptor antagonist refers to a compound that binds to a PAF receptor with a binding constant of 30 $\mu$M or lower.

The term 5-lipoxygenase inhibitor refers to a compound that inhibits the enzyme at 30 $\mu$M or lower in a broken cell system.

The term pharmaceutically active derivative refers to any compound that upon administration to the recipient, is capable of providing directly or indirectly, the compounds disclosed herein.

The 2,5-diaryl tetrahydrothiophenes, pyrrolidines, and tetrahydrofurans, 1,3 diaryl cyclopentanes, and the 2,4-diaryl tetrahydrothiophenes, pyrrolidines and tetrahydrofurans of the above-defined formulas exhibit PAF receptor antagonist activity or inhibit the enzyme 5-lipoxygenase, or have dual activity, and are thus useful in the treatment of humans who have immune and allergic disorders that are mediated by PAF or products of 5-lipoxygenase.

The following are nonlimiting examples of compounds that fall within Formulas I, II, and III. These examples are merely exemplary and are not intended to limit the scope of the invention.

Formula I

Cis and Trans Isomers of the Following Compounds N-Alkyl/arylhydroxyureas:

2-[5-(N'-Ethyl-N'-hydroxyureidyl)-4-(p-bromophenylthioethoxy)-3-methoxyphenyl]-5-(3,4,5-trimethoxyphenyl)-tetrahydrofuran 2-[5-(N'-Butyl-N'-hydroxyureidyl)-4-(2-bromophenylthioethoxy)-3-methoxyphenyl]-5-(3,4,5-trimethoxyphenyl)-tetrahydrofuran 2-[5-(N'-Butyl-N'-hydroxyureidyl)-4-(3-bromophenylthioethoxy)-3-methoxyphenyl]-5-(3,4,5-trimethoxyphenyl)-tetrahydrofuran 2-[5-(N'-Butyl-N'-hydroxyureidyl)-4-(3,4-dichlorophenylthioethoxy)-3-methoxyphenyl]-5-(3,4,5-trimethoxyphenyl)-tetrahydrofuran 2-[5-(N'-Butyl-N'-hydroxyureidyl)-4-(p-chlorophenylthioethoxy)-3-methoxyphenyl]-5-(3,4,5-trimethoxyphenyl)-tetrahydrofuran 2-[5-(N'-Butyl-N'-hydroxyureidyl)-4-(p-fluorophenylthioethoxy)-3-methoxyphenyl]-5-(3,4,5-trimethoxyphenyl)-tetrahydrofuran 2-[5-(N'-Butyl-N'-hydroxyureidyl)-4-(2,3,5,6-tetrafluorophenylthioethoxy)-3-methoxyphenyl]-5-(3,4,5-trimethoxyphenyl)-tetrahydrofuran 2-[5-(N'-Butyl-N'-hydroxyureidyl)-4-(2,3,4,5-tetrafluorophenylethoxy)-3-methoxyphenyl]-5-(3,4,5-trimethoxyphenyl)-tetrahydrofuran 2-[5-(N'-Butyl-N'-hydroxyureidyl)-4-(p-bromophenysulfonylethoxy)-3-methoxyphenyl]-5-(3,4,5-trimethoxyphenyl)-tetrahydrofuran 2-[5-(N'-Butyl-N'-hydroxyureidyl)-4-(2-bromophenylsulfonylethoxy)-3-methoxyphenyl]-5-(3,4,5-trimethoxyphenyl)-tetrahydrofuran
2-[5-(N'-Hydroxy-N'-methylureidyl)-4-(p-bromophenylthioethoxy)-3-methoxyphenyl]-5-(3,4,5-trimethoxyphenyl)-tetrahydrofuran
2-[5-(N'-Hydroxy-N'-methylureidyl)-4-(2-bromophenylthioethoxy)-3-methoxyphenyl]-5-(3,4,5-trimethoxyphenyl)-tetrahydrofuran
2-[5-(N'-Hydroxy-N'-methylureidyl)-4-(3-bromophenylthioethoxy)-3-methoxyphenyl]-5-(3,4,5-trimethoxyphenyl)-tetrahydrofuran
2-[5-(N'-Hydroxy-N'-methylureidyl)-4-(3,4-dichlorophenylthioethoxy)-3-methoxyphenyl]-5-(3,4,5-trimethoxyphenyl)-tetrahydrofuran
2-[5-(N'-Hydroxy-N'-methylureidyl)-4-(p-chlorophenylthioethoxy)-3-methoxyphenyl]-5-(3,4,5-trimethoxyphenyl)-tetrahydrofuran
2-[5-(N'-Ethyl-N'-hydroxyureidyl)-4-p-fluorophenylthioethoxy)-3-methoxyphenyl]-5-(3,4,5-trimethoxyphenyl)-tetrahydrofuran
2-[5-(N'-Ethyl-N'-hydroxyureidyl)-4-(2,3,5,6-tetrafluorphenylthioethoxy)-3-methoxyphenyl]-5-(3,4,5-trimethoxyphenyl)-tetrahydrofuran
2-[5-(N'-Ethyl-N'-hydroxyureidyl)-4-(2,3,4,5-tetrafluorophenylethoxy)-3-methoxyphenyl]-5-(3,4,5-trimethoxyphenyl)-tetrahydrofuran
2-[5-(N'-Ethyl-N'-hydroxyureidyl)-4-(2,3,4,5-tetrafluorophenylethoxy)-3-methoxyphenyl]-5-(3,4,5-trimethoxyphenyl)-tetrahydrofuran
2-[5-(N'-p-Chlorophenyl-N'-hydroxyureidyl)-4-(2-bromophenylsulfonylethoxy)-3-methoxyphenyl]-5-(3,4,5-trimethoxyphenyl)-tetrahydrofuran
2-[5-(N'-p-Chlorophenyl-N'-hydroxyureidyl)-4-(p-bromophenylthioethoxy)-3-methoxyphenyl]-5-(3,4,5-trimethoxyphenyl)-tetrahydrofuran
2-[5-(N'-tert-Butyl-N'-hydroxyureidyl)-4-(p-bromophenylthioethoxy)-3-methoxyphenyl]-5-(3,4,5-trimethoxyphenyl)-tetrahydrofuran
2-[5-(N'-tert-Butyl-N'-hydroxyureidyl)-4-(2-bromophenylthioethoxy)-3-methoxyphenyl]-5-(3,4,5-trimethoxyphenyl)-tetrahydrofuran
2-[5-(N'-tert-Butyl-N'-hydroxyureidyl)-4-(3-bromophenylthioethoxy)-3-methoxyphenyl]-5-(3,4,5-trimethoxyphenyl)-tetrahydrofuran
2-[5-(N'-Cyclohexyl-N'-hydroxyureidyl)-4-(3,4-dichlorophenylthioethoxy)-3-methoxyphenyl]-5-(3,4,5-trimethoxyphenyl)-tetrahydrofuran
2-[5-(N'-Cyclohexyl-N'-hydroxyureidyl)-4-(p-chlrophenylthioethoxy)-3-methoxyphenyl]-5-(3,4,5-trimethoxyphenyl)-tetrahydrofuran
2-[5-(N'-Cyclohexyl-N'-hydroxyureidyl)-4-(p-fluorophenylthioethoxy)-3-methoxyphenyl]-5-(3,4,5-trimethoxyphenyl)-tetrahydrofuran
2-[5-(N'-Benzyl-N'-hydroxyureidyl)-4-(2,3,5,6-tetrafluorophenylthioethoxy)-3-methoxyphenyl]-5-(3,4,5-trimethoxyphenyl)-tetrahydrofuran
2-[5-(N'-Benzyl-N'-hydroxyureidyl)-4-(2,3,4,5-tetrafluorophenylethoxy)-3-methoxyphenyl]-5-(3,4,5-trimethoxyphenyl)-tetrahydrofuran
2-[5-(N'-Benzyl-N'-hydroxyureidyl)-4-(p-bromophenylsulfonylethoxy)-3-methoxyphenyl]-5-(3,4,5-trimethoxyphenyl)-tetrahydrofuran
2-[5-(N'-Benzyl-N'-hydroxyureidyl)-4-(2-bromophenylsulfonylethoxy)-3-methoxyphenyl]-5-(3,4,5-trimethoxyphenyl)-tetrahydrofuran
2-[5-(N'-Hydroxy-N'-i-propylureidyl)-4-(p-bromophenylthioethoxy)-3-methoxyphenyl]-5-(3,4,5-trimethoxyphenyl)-tetrahydrofuran
2-[5-(N'-sec-Butyl-N'-hydroxyureidyl)-4-(p-bromophenylthioethoxy)-3-methoxyphenyl]-5-(3,4,5-trimethoxyphenyl)-tetrahydrofuran
2-[5-(N'-sec-Butyl-N'-hydroxyureidyl)-4-(2-bromophenylthioethoxy)-3-methoxyphenyl]-5-(3,4,5-trimethoxyphenyl)-tetrahydrofuran
2-[5-(N'-Hydroxy-N'-propylureidyl)-4-(3-bromophenylthioethoxy)-3-methoxyphenyl]-5-(3,4,5-trimethoxyphenyl)-tetrahydrofuran
2-[5-(N'-Hydroxy-N'-n-pentylureidyl)-4-(3,4-dichlorophenylthioethoxy)-3-methoxyphenyl]-5-(3,4,5-trimethoxyphenyl)-tetrahydrofuran
2-[5-(N'-Hexyl-N'-hydroxyureidyl)-4-(p-chlorophenylthioethoxy)-3-methoxyphenyl]-5-(3,4,5-trimethoxyphenyl)-tetrahydrofuran
2-[5-(N'-Hydroxy-N'-octylureidyl)-4-(p-fluorophenylthioethoxy)-3-methoxyphenyl]-5-(3,4,5-trimethoxyphenyl)-tetrahydrofuran
2-[5-(N'-Hydroxy-methoxyethylureidyl)-4-(2,3,5,6-tetrafluorophenylthioethoxy)-3-methoxyphenyl]-5-(3,4,5-trimethoxyphenyl)-tetrahydrofuran
2-[5-(N'-Decyl-N'-hydroxyureidyl)-4-(2,3,4,5-tetrafluorophenylethoxy)-3-methoxyphenyl]-5-(3,4,5-trimethoxyphenyl)-tetrahydrofuran
2-[5-(N'-Hydroxy-N'-methylureidylmethyl)-4-(p-chlorophenylthioethoxy)-3-methoxyphenyl]-5-(3,4,5-trimethoxyphenyl)-tetrahydrofuran
2-[5-(N'-Hydroxy-N'-i-propylureidylmethyl)-4-(p-chlorophenylthioethoxy)-3-methoxyphenyl]-5-(3,4,5-trimethoxyphenyl)-tetrahydrofuran
2-[5-(N'-Butyl-N'-hydroxyureidylmethyl)-4-(p-chlorophenylthioethoxy)-3-methoxyphenyl]-5-(3,4,5-trimethoxyphenyl)-tetrahydrofuran
2-[5-(N'-Hydroxy-N'-propylureidylmethyl)-4-(p-chlorophenylthioethoxy)-3-methoxyphenyl]-5-(3,4,5-trimethoxyphenyl)-tetrahydrofuran
2-[5-(N'-Ethyl-N'-hydroxyureidylmethyl)-4-(p-chlorophenylthioethoxy)-3-methoxyphenyl]-5-(3,4,5-trimethoxyphenyl)-tetrahydrofuran
2-[5-(N'-Hydroxy-N'-octylureidylmethyl)-4-(p-chlorophenylthioethoxy)-3-methoxyphenyl]-5-(3,4,5-trimethoxyphenyl)-tetrahydrofuran
2-[5-(N'-Benzyl-N'-hydroxyureidyl)-4-(p-bromophenylsulfonylethoxy)-3-methoxyphenyl]-5-(3,4,5-trimethoxyphenyl)-tetrahydrothiophene
2-[5-(N'-Benzyl-N'-hydroxyureidyl)-4-(2-bromophenylsulfonylethoxy)-3-methoxyphenyl]-5-(3,4,5-trimethoxyphenyl)-tetrahydrothiophene
2-[5-(N'-Hydroxy-N'-i-propylureidyl)-4-(p-bromophenylthioethoxy)-3-methoxyphenyl]-5-(3,4,5-trimethoxyphenyl)-tetrahydrothiophene
2-[5-(N'-Hydroxyl-N'-octylureidyl)-4-(p-fluorophenylthioethoxy)-3-methoxyphenyl]-5-(3,4,5-trimethoxyphenyl)-tetrahydrothiophene
2-[5-(N'-Butyl-N'-hydroxyureidyl)-4-(p-bromophenylthioethoxy)-3-methoxyphenyl]-5-(3,4,5-trimethoxyphenyl)-tetrahydrothiophene
2-[5-(N'-Butyl-N'-hydroxyureidyl)-4-(2-bromophenylthioethoxy)-3-methoxyphenyl]-5-(3,4,5-trimethoxyphenyl)-tetrahydrothiophene
2-[5-(N'-Butyl-N'-hydroxyureidyl)-4-(3-bromophenylthioethoxy)-3-methoxyphenyl]-5-(3,4,5-trimethoxyphenyl)-tetrahydrothiophene
2-[5-(N'-Hydroxy-N'-methylureidylmethyl)-4-(p-chlorophenylthioethoxy)-3-methoxyphenyl]-5-(3,4,5-trimethoxyphenyl)-tetrahydrothiophene
2-[5-(N'-Hydroxy-N'-i-propylureidylmethyl)-4-(p-chlorophenylthioethoxy)-3-methoxyphenyl]-5-(3,4,5-trimethoxyphenyl)-tetrahydrothiophene 2-[5-(N'-Butyl-N'-hydroxyureidylmethyl)-4-(p-chlorophenylthioethoxy)-3-methoxyphenyl]-5-(3,4,5-trimethoxyphenyl)-tetrahydrothiophene Triple Bonded Hydroxamates:

2-[5-[1-(N-Acetyl-N-hydroxyamino)propyn-3-yl]-4-(p-bromophenylthioethoxy)-3-methoxyphenyl]-5-(3,4,5-trimethoxyphenyl)-tetrahydrofuran 2-[5-[1-(N-Hydroxy-N-propanoylamino)propyn-3-yl]-4-(p-chlorophenylthioethoxy)-3-methoxyphenyl]-5-(3,4,5-trimethoxyphenyl)-tetrahydrofuran 2-[5-[1-(N-Butanoyl-N-hydroxyamino)propyn-3-yl]-4-(3,4-dichlorophenylthioethoxy)-3-methoxyphenyl]-5-(3,4,5-trimethoxyphenyl)-tetrahydrofuran 2-[5-[1-(N-Hydroxy-N-cyclohexanecarbonylamino)propyn-3-yl]-4-(p-fluorophenylthioethoxy)-3-methoxyphenyl]-5-(3,4,5-trimethoxyphenyl)-tetrahydrofuran 2-[5-[1-(N-Hydroxy-N-3-phenoxybenzoylamino)propyn-3-yl]-4-(2,3,5,6-tetrafluorophenylthioethoxy)-3-methoxyphenyl]-5-(3,4,5-trimethoxyphenyl)-tetrahydrofuran 2-[5-[1-(N-Hydroxy-N-methoxybenzoylamino)propyn-3-yl]-4-(2-bromophenylthioethoxy)-3-methoxyphenyl]-5-(3,4,5-trimethoxyphenyl)-tetrahydrofuran 2-[5-[1-(N-Hydroxy-N-hydroxybenzoylamino)propyn-3-yl]-4-(p-chlorophenylthioethoxy)-3-methoxyphenyl]-5-(3,4,5-trimethoxyphenyl)-tetrahydrofuran Triple Bonded Ureas:

2-[5-[1-(N'-Hydroxy-N'-methylureidyl)propyn-3-yl]-4-(p-chlorophenylthioethoxy)-3-methoxyphenyl]-5-(3,4,5-trimethoxyphenyl)-tetrahydrofuran 2-[5-[1-(N'-Ethyl-N'-hydroxyureidyl)propyn-3-yl]-4-(p-chlorophenylthioethoxy)-3-methoxyphenyl]-5-(3,4,5-trimethoxyphenyl)-tetrahydrofuran 2-[5-[1-(N'-Hydroxy-N'-propylureidyl)propyn-3-yl]-4-(p-chlorophenylthioethoxy)-3-methoxyphenyl]-5-(3,4,5-trimethoxyphenyl)-tetrahydrofuran 2-[5-[1-(N'-n-Butyl-N'-hydroxyureidyl)propyn-3-yl]-4-(p-chlorophenylthioethoxy)-3-methoxyphenyl]-5-(3,4,5-trimethoxyphenyl)-tetrahydrofuran 2-[5-[1-(N'-Hydroxy-N'-i-propylureidyl)propyn-3-yl]-4-(p-chlorophenylthioethoxy)-3-methoxyphenyl]-5-(3,4,5-trimethoxyphenyl)-tetrahydrofuran 2-[5-[1-(N'-tert-Butyl-N'-hydroxyureidyl)propyn-3-yl]-4-(p-chlorophenylthioethoxy)-3-methoxyphenyl]-5-(3,4,5-trimethoxyphenyl)-tetrahydrofuran 2-[5-[1-(N'-Benzyl-N'-hydroxyureidyl)propyn-3-yl]-4-(p-chlorophenylthioethoxy)-3-methoxyphenyl]-5-(3,4,5-trimethoxyphenyl)-tetrahydrofuran 2-[5-[1-(N'-Cyclopropylmethyl-N'-hydroxyureidyl)propyn-3-yl]-4-(p-chlorophenylthioethoxy)-3-methoxyphenyl]-5-(3,4,5-trimethoxyphenyl)-tetrahydrofuran 2-[5-[1-(N'-Allyl-N'-hydroxyureidyl)propyn-3-yl]-4-(p-chlorophenylthioethoxy)-3-methoxyphenyl]-5-(3,4,5-trimethoxyphenyl)-tetrahydrofuran 2-[5-[1-(N'-Hydroxy-N'-hydroxyethylureidyl)propyn-3-yl]-4-(p-chlorophenylthioethoxy)-3-methoxyphenyl]-5-(3,4,5-trimethoxyphenyl)-tetrahydrofuran Double Bonded Hydroxamates: Both Cis and Trans Isomers at the Tetrahydrofuran Ring 2-[5-[trans-1-(N-Acetyl-N-hydroxyamino)propen-3-yl]-4-(p-bromophenylthioethoxy)-3-methoxyphenyl]-5-3,4,5-trimethoxyphenyl)tetrahydrofuran 2-[5-[trans-1-(N-Hydroxy-N-propanoylamino)propen-3-yl]-4-(p-chlorophenylthioethoxy)-3-methoxyphenyl]-5-(3,4,5-trimethoxyphenyl)tetrahydrofuran 2-[5-[trans-1-(N-Butanoyl-N-hydroxyamino)propen-3-yl]-4-(3,4-dichlorophenylthioethoxy)-3-methoxyphenyl]-5-(3,4,5-trimethoxyphenyl)tetrahydrofuran 2-[5-[trans-1-(N-Hydroxy-N-cyclohexanecarbonylamino)propen-3-yl]-4-(p-fluorophenylthioethoxy)-3-methoxyphenyl]-5-(3,4,5-trimethoxyphenyl)tetrahydrofuran 2-[5-[trans-1-(N-Hydroxy-N-phenoxybenzoylamino)propen-3-yl]-4-(2,3,5,6-tetrafluorophenylthioethoxy)-3-methoxyphenyl]-5-(3,4,5-trimethoxyphenyl)tetrahydrofuran 2-[5-[trans-1-(N-Hydroxy-N-methoxybenzoylamino)propen-3-yl]-4-(p-bromophenylthioethoxy)-3-methoxyphenyl]-5-(3,4,5-trimethoxyphenyl)tetrahydrofuran 2-[5-[trans-1-(N-Hydroxy-N-hydroxybenzoylamino)propen-3-yl]-4-(p-chlorophenylthioethoxy)-3-methoxyphenyl]-5-(3,4,5-trimethoxyphenyl)tetrahydrofuran Double Bonded Ureas: Both Cis and Trans Isomers at the Tetrahydrofuran Ring.

2-[5-[trans-1-(N'-Hydroxy-N'-methylureidyl)propen-3-yl]-4-(p-chlorophenylthioethoxy)-3-methoxyphenyl]-5-(3,4,5-trimethoxyphenyl)tetrahydrofuran 2-[5-[trans-1-(N'-Ethyl-N'-hydroxyureidyl)propen-3-yl]-4-(p-chlorophenylthioethoxy)-3-methoxyphenyl]-5-(3,4,5-trimethoxyphenyl)tetrahydrofuran 2-[5-[trans-1-(N'-Hydroxy-N'-propylureidyl)propen-3-yl]-4-(p-chlorophenylthioethoxy)-3-methoxyphenyl]-5-(3,4,5-trimethoxyphenyl)tetrahydrofuran 2-[5-[trans-1-(N'-n-Butyl-N'-hydroxyureidyl)propen-3-yl]-4-(p-chlorophenylthioethoxy)-3-methoxyphenyl]-5-(3,4,5-trimethoxyphenyl)tetrahydrofuran 2-[5-[trans-1-(N'-Hydroxy-N'-i-propylureidyl)propen-3-yl]-4-(p-chlorophenylthioethoxy)-3-methoxyphenyl]-5-(3,4,5-trimethoxyphenyl)tetrahydrofuran 2-[5-[trans-1-(N'-tert-Butyl-N'-hydroxyureidyl)propen-3-yl]-4-(p-chlorophenylthioethoxy)-3-methoxyphenyl]-5-(3,4,5-trimethoxyphenyl)tetrahydrofuran 2-[5-[trans-1-(N'-Benzyl-N'-hydroxyureidyl)propen-3-yl]-4-(p-chlorophenylthioethoxy)-3-methoxyphenyl]-5-(3,4,5-trimethoxyphenyl)tetrahydrofuran 2-[5-[trans-1-(N'-Cyclopropylmethyl-N'-hydroxyureidyl)propen-3-yl]-4-(p-chlorophenylthioethoxy)-3-methoxyphenyl]-5-(3,4,5-trimethoxyphenyl)tetrahydrofuran 2-[5-[trans-1-(N'-Allyl-N'-hydroxyureidyl)propen-3-yl]-4-(p-chlorophenylthioethoxy)-3-methoxyphenyl]-5-(3,4,5-trimethoxyphenyl)tetrahydrofuran 2-[5-[trans-1-(N'-Hydroxy-N'-hydroxyethlureidyl)propen-3-yl]-4-(p-chlorophenylthioethoxy)-3-methoxyphenyl]-5-(3,4,5-trimethoxyphenyl)-tetrahydrofuran Formula II Cis and Trans Isomers of the Following Compounds N-Alkyl/arylhydroxyureas:

4-[5-(N'-Butyl-N'-hydroxyureidyl)-4-(p-bromophenylthioethoxy)-3-methoxyphenyl]-2-(3,4,5-trimethoxyphenyl)-tetrahydrofuran 4-[5-(N'-Butyl-N'-hydroxyureidyl)-4-(2-bromophenylthioethoxy)-3-methoxyphenyl]-2-(3,4,5-trimethoxyphenyl)-tetrahydrofuran 4-[5-(N'-Butyl-N'-hydroxyureidyl)-4-(3-bromophenylthioethoxy)-3-methoxyphenyl]-2-(3,4,5-trimethoxyphenyl)-tetrahydrofuran 4-[5-(N'-Butyl-N'-hydroxyureidyl)-4-(3,4-dichlorophenylthioethoxy)-3-methoxyphenyl]-2-(3,4,5-trimethoxyphenyl)-tetrahydrofuran 4-[5-(N'-Butyl-N'-hydroxyureidyl)-4-(p-chlorophenylthioethoxy)-3-methoxyphenyl]-2-(3,4,5-trimethoxyphenyl)-tetrahydrofuran 4-[5-(N'-Butyl-N'-hydroxyureidyl)-4-(p-fluorophenylthioethoxy)-3-methoxyphenyl]-2-(3,4,5-trimethoxyphenyl)-tetrahydrofuran 4-[5-(N'-Butyl-N'-hydroxyureidyl)-4-(2,3,5,6-tetrafluorophenylthioethoxy)-3-methoxyphenyl]-2-(3,4,5-trimethoxyphenyl)-tetrahydrofuran 4-[5-(N'-Butyl-N'-hydroxyureidyl)-4-(2,3,4,5-tetrafluorophenylethoxy)-3-methoxyphenyl]-2-(3,4,5-trimethoxyphenyl)-tetrahydrofuran 4-[5-(N'-Butyl-N'-hydroxyureidyl)-4-(p-bromophenylsulfonylethoxy)-3-methoxyphenyl]-2-(3,4,5-trimethoxyphenyl)-tetrahydrofuran 4-[5-(N'-Butyl-N'-hydroxyureidyl)-4-(2-bromophenylsulfonylethoxy)-3-methoxyphenyl]-2-(3,4,5-trimethoxyphenyl)-tetrahydrofuran 4-[5-(N'-Hydroxy-N'-methylureidyl)-4-(p-bromophenylthioethoxy)-3-methoxyphenyl]-2-(3,4,5-trimethoxyphenyl)-tetrahydrofuran 4-[5-(N'-Hydroxy-N'-methylureidyl)-4-(2-bromophenylthioethoxy)-3-methoxyphenyl]-2-(3,4,5-trimethoxyphenyl)-tetrahydrofuran 4-[5-(N'-Hydroxy-N'-methylureidyl)-4-(3-bromophenylthioethoxy)-3-methoxyphenyl]-2-(3,4,5-trimethoxyphenyl)-tetrahydrofuran 4-[5-(N'-Hydroxy-N'-methylureidyl)-4-(3,4-dichlorophenylthioethoxy)-3-methoxyphenyl]-2-(3,4,5-trimethoxyphenyl)-tetrahydrofuran 4-[5-(N'-Hydroxy-N'-methylureidyl)-4-(p-chlorophenylthioethoxy)-3-methoxyphenyl]-2-(3,4,5-trimethoxyphenyl)-tetrahydrofuran 4-[5-(N'-Ethyl-N'-hydroxyureidyl)-4-(p-fluorophenylthioethoxy)-3-methoxyphenyl]-2-(3,4,5-trimethoxyphenyl)-tetrahydrofuran 4-[5-(N'-Ethyl-N'-hydroxyureidyl)-4-(2,3,5,6-tetrafluorophenylthioethoxy)-3-methoxyphenyl]-2-(3,4,5-trimethoxyphenyl)-tetrahydrofuran 4-[5-(N'-Ethyl-N'-hydroxyureidyl)-4-(2,3,4,5-tetrafluorophenylethoxy)-3-methoxyphenyl]-2-(3,4,5-trimethoxyphenyl)-tetrahydrofuran 4-[5-(N'-Ethyl-N'-hydroxyureidyl)-4-(p-bromophenylsulfonylethoxy)-3-methoxyphenyl]-2-(3,4,5-trimethoxyphenyl)-tetrahydrofuran 4-[5-(N'-p-Chlorophenyl-N'-hydroxyureidyl)-4-(2-bromophenylsulfonylethoxy)-3-methoxyphenyl]-2-(3,4,5-trimethoxyphenyl)-tetrahydrofuran 4-[5-(N'-p-Chlorophenyl-N'-hydroxyureidyl)-4-(p-bromophenylthioethoxy)-3-methoxyphenyl]-2-(3,4,5-trimethoxyphenyl)-tetrahydrofuran 4-[5-(N'-tert-Butyl-N'-hydroxyureidyl)-4-(p-bromophenylthioethoxy)-3-methoxyphenyl]-2-(3,4,5-trimethoxyphenyl)-tetrahydrofuran 4-[5-(N'-tert-Butyl-N'-hydroxyureidyl)-4-(2-bromophenylthioethoxy)-3-methoxyphenyl]-2-(3,4,5-trimethoxyphenyl)-tetrahydrofuran 4-[5-(N'-tert-Butyl-N'-hydroxyureidyl)-4-(3-bromophenylthioethoxy)-3-methoxyphenyl]-2-(3,4,5-trimethoxyphenyl)-tetrahydrofuran 4-[5-(N'-Cyclohexyl-N'-hydroxyureidyl)-4-(3,4-dichlorophenylthioethoxy)-3-methoxyphenyl]-2-(3,4,5-trimethoxyphenyl)-tetrahydrofuran 4-[5-(N'-Cyclohexyl-N'-hydroxyureidyl)-4-(p-chlorophenylthioethoxy)-3-methoxyphenyl]-2-(3,4,5-trimethoxyphenyl)-tetrahydrofuran 4-[5-(N'-Cyclohexyl-N'-hydroxyureidyl)-4-(p-fluorophenylthioethoxy)-3-methoxyphenyl]-2-(3,4,5-trimethoxyphenyl)-tetrahydrofuran 4-[5-(N'-Benzyl-N'-hydroxyureidyl)-4-(2,3,5,6-tetrafluorophenylthioethoxy)-3-methoxyphenyl]-2-(3,4,5-trimethoxyphenyl)-tetrahydrofuran 4-[5-(N'-Benzyl-N'-hydroxyureidyl)-4-(2,3,4,5-tetrafluorophenylethoxy)-3-methoxyphenyl]-2-(3,4,5-trimethoxyphenyl)-tetrahydrofuran 4-[5-(N'-Benzyl-N'-hydroxyureidyl)-4-(p-bromophenylsulfonylethoxy)-3-methoxyphenyl]-2-(3,4,5-trimethoxyphenyl)-tetrahydrofuran 4-[5-(N'-Benzyl-N'-hydroxyureidyl)-4-(2-bromophenylsulfonylethoxy)-3-methoxyphenyl]-2-(3,4,5-trimethoxyphenyl)-tetrahydrofuran 4-[5-(N'-Hydroxy-N'-i-propylureidyl)-4-(p-bromophenylthioethoxy)-3-methoxyphenyl]-2-(3,4,5-trimethoxyphenyl)-tetrahydrofuran 4-[5-(N'-sec-Butyl-N'-hydroxyureidyl)-4-(p-bromophenylthioethoxy)-3-methoxyphenyl]-2-(3,4,5-trimethoxyphenyl)-tetrahydrofuran 4-[5-(N'-sec-Butyl-N'-hydroxyureidyl)-4-(2-bromophenylthioethoxy)-3-methoxyphenyl]-2-(3,4,5-trimethoxyphenyl)-tetrahydrofuran 4-[5-(N'-Hydroxy-N'-propylureidyl)-4-(3-bromophenylthioethoxy)-3-methoxyphenyl]-2-(3,4,5-trimethoxyphenyl)-tetrahydrofuran 4-[5-(N'-Hydroxy-N'-n-pentylureidyl)-4-(3,4-dichlorophenylthioethoxy)-3-methoxyphenyl]-2-(3,4,5-trimethoxyphenyl)-tetrahydrofuran 4-[5-(N'-Hexyl-N'-hydroxyureidyl)-4-(p-chlorophenylthioethoxy)-3-methoxyphenyl]-2-(3,4,5-trimethoxyphenyl)-tetrahydrofuran 4-[5-(N'-Hydroxy-N'-octylureidyl)-4-(p-fluorophenylthioethoxy)-3-methoxyphenyl]-2-(3,4,5-trimethoxyphenyl)-tetrahydrofuran 4-[5-(N'-Hydroxy-N'-methoxyethylureidyl)-4-(2,3,5,6-tetrafluorophenylthioethoxy)-3-methoxyphenyl]-2-(3,4,5-trimethoxyphenyl)-tetrahydrofuran 4-[5-(N'-Decyl-N'-hydroxyureidyl)-4-(2,3,4,5-tetrafluorophenylethoxy)-3-methoxyphenyl]-2-(3,4,5-trimethoxyphenyl)-tetrahydrofuran 4-[5-(N'-Hydroxy-N'-methylureidylmethyl)-4-(p-chlorophenylthioethoxy)-3-methoxyphenyl]-2-(3,4,5-trimethoxyphenyl)-tetrahydrofuran 4-[5-(N'-Hydroxy-N'-i-propylureidylmethyl)-4-(p-chlorophenylthioethoxy)-3-methoxyphenyl]-2-(3,4,5-trimethoxyphenyl)-tetrahydrofuran 4-[5-(N'-Butyl-N'-hydroxyureidylmethyl)-4-(p-chlorophenylthioethoxy)-3-methoxyphenyl]-2-(3,4,5-trimethoxyphenyl)-tetrahydrofuran 4-[5-(N'-Hydroxy-N'-propylureidylmethyl)-4-(p-chlorophenylthioethoxy)-3-methoxyphenyl]-2-(3,4,5-trimethoxyphenyl)-tetrahydrofuran 4-[5-(N'-Ethyl-N'-hydroxyureidylmethyl)-4-(p-chlorophenylthioethoxy)-3-methoxyphenyl]-2-(3,4,5-trimethoxyphenyl)-tetrahydrofuran 4-[5-(N'-Hydroxy-N'-octylureidylmethyl)-4-(p-chlorophenylthioethoxy)-3-methoxyphenyl]-2-(3,4,5-trimethoxyphenyl)-tetrahydrofuran 4-[5-(N'-Benzyl-N'-hydroxyureidyl)-4-(p-bromophenylsulfonylethoxy)-3-methoxyphenyl]-2-(3,4,5-trimethoxyphenyl)-tetrahydrofuran 4-[5-(N'-Benzyl-N'-hydroxyureidyl)-4-(2-bromophenylsulfonylethoxy)-3-methoxyphenyl]-2-(3,4,5-trimethoxyphenyl)-tetrahydrofuran 4-[5-(N'-Hydroxy-N'-i-propylureidyl)-4-(p-bromophenylthioethoxy)-3-methoxyphenyl]-2-(3,4,5-trimethoxyphenyl)-tetrahydrofuran 4-[5-(N'-Hydroxy-N'-octylureidyl)-4-(p-fluorophenylthioethoxy)-3-methoxyphenyl]-2-(3,4,5-trimethoxyphenyl)-tetrahydrofuran 4-[5-(N'-Butyl-N'-hydroxyureidyl)-4-(p-bromophenylthioethoxy)-3-methoxyphenyl]-2-(3,4,5-trimethoxyphenyl)-tetrahydrofuran 4-[5-(N'-Butyl-N'-hydroxyureidyl)-4-(2-bromophenylthioethoxy)-3-methoxyphenyl]-2-(3,4,5-trimethoxyphenyl)-tetrahydrofuran 4-[5-(N'-Butyl-N'-hydroxyureidyl)-4-(3-bromophenylthioethoxy)-3-methoxyphenyl]-2-(3,4,5-trimethoxyphenyl)-tetrahydrofuran 4-[5-(N'-Hydroxy-N'-methylureidylmethyl)-4-(p-chlorophenylthioethoxy)-3-methoxyphenyl]-2-(3,4,5-trimethoxyphenyl)-tetrahydrofuran 4-[5-(N'-Hydroxy-N'-i-propylureidylmethyl)-4-(p-chlorophenylthioethoxy)-3-methoxyphenyl]-2-(3,4,5-trimethoxyphenyl)-tetrahydrofuran 4-[5-(N'-Butyl-N'-hydroxyureidylmethyl)-4-(p-chlorophenylthioethoxy)-3-methoxyphenyl]-2-(3,4,5-trimethoxyphenyl)-tetrahydrofuran Triple Bonded Hydroxamates:

4-[5-[1-(N-Acetyl-N-hydroxyamino)propyn-3-yl]-4-(p-bromophenylthioethoxy)-3-methoxyphenyl]-2-(3,4,5-trimethoxyphenyl)-tetrahydrofuran 4-[5-[1-(N-Hydroxy-N-propanoylamino)propyn-3-yl]-4-(p-chlorophenylthioethoxy)-3-methoxyphenyl]-2-(3,4,5-trimethoxyphenyl)-tetrahydrofuran 4-[5-[1-(N-Butanoyl-N-hydroxyamino)propyn-3-yl]-4-(3,4-dichlorophenylthioethoxy)-3-methoxyphenyl]-2-(3,4,5-trimethoxyphenyl)-tetrahydrofuran 4-[5-[1-(N-Hydroxy-N-cyclohexanecarbonylamino)propyn-3-yl]-4-(p-fluorophenylthioethoxy)-3-methoxyphenyl]-2-(3,4,5-trimethoxyphenyl)-tetrahydrofuran 4-[5-[1-(N-Hydroxy-N-phenoxybenzoylamino)propyn-3-yl]-4-(2,3,5,6-tetrafluorophenylthioethoxy)-3-methoxyphenyl]-2-(3,4,5-trimethoxyphenyl)-tetrahydrofuran 4-[5-[1-(N-Hydroxy-N-methoxybenzoylamino)propyn-3-yl]-4-(2-bromophenylthioethoxy)-3-methoxyphenyl]-2-(3,4,5-trimethoxyphenyl)-tetrahydrofuran 4-[5-[1-(N-Hydroxy-N-hydroxybenzoylamino)propyn-3-yl]-4-(p-chlorophenylthioethoxy)-3-methoxyphenyl]-2-(3,4,5-trimethoxyphenyl)-tetrahydrofuran Triple Bonded Ureas:

4-[5-[1-(N'-Hydroxy-N'-methylureidyl)propyn-3-yl]-4-(p-chlorophenylthioethoxy)-3-methoxyphenyl]-2-(3,4,5-trimethoxyphenyl)-tetrahydrofuran 4-[5-[1-(N'-Ethyl-N'-hydroxyureidyl)propyn-3-yl]-4-(p-chlorophenylthioethoxy)-3-methoxyphenyl]-2-(3,4,5-trimethoxyphenyl)-tetrahydrofuran 4-[5-[1-(N'-Hydroxy-N'-propylureidyl)propyn-3-yl]-4-p-chlorophenylthioethoxy)-3-methoxyphenyl]-2-(3,4,5-trimethoxyphenyl)-tetrahydrofuran 4-[5-[1-(N'-n-Butyl-N'-hydroxyureidyl)propyn-3-yl]-4-(p-chlorophenylthioethoxy)-3-methoxyphenyl]-2-(3,4,5-trimethoxyphenyl)-tetrahydrofuran 4-[5-[1-(N'-Hydroxy-N'-i-propylureidyl)propyn-3-yl]-4-(p-chlorophenylthioethoxy)-3-methoxyphenyl]-2-(3,4,5-trimethoxyphenyl)-tetrahydrofuran 4-[5-[1-(N'-tert-Butyl-N'-hydroxyureidyl)propyn-3-yl]-4-(p-chlorophenylthioethoxy)-3-methoxyphenyl]-2-(3,4,5-trimethoxyphenyl)-tetrahydrofuran 4-[5-[1-(N'-Benzyl-N'-hydroxyureidyl)propyn-3-yl]-4-(p-chlorophenylthioethoxy)-3-methoxyphenyl]-2-(3,4,5-trimethoxyphenyl)-tetrahydrofuran 4-[5-[1-(N'-Cyclopropylmethyl-N'-hydroxyureidyl)propyn-3-yl]-4-(p-chlorophenylthioethoxy)-3-methoxyphenyl]-2-(3,4,5-trimethoxyphenyl)-tetrahydrofuran 4-[5-[1-(N'-Allyl-N'-hydroxyureidyl)propyn-3-yl]-4-(p-chlorophenylthioethoxy)-3-methoxyphenyl]-2-(3,4,5-trimethoxyphenyl)-tetrahydrofuran 4-[5-[1-(N'-Hydroxy-N'-hydroxyethylureidyl)propyn-3-yl]-4-(p-chlorophenylthioethoxy)-3-methoxyphenyl]-2-(3,4,5-trimethoxyphenyl)-tetrahydrofuran Double Bonded Hydroxamates: Both Cis and Trans Isomers at the Tetrahydrofuran Ring.

4-[5-[trans-1-(N-Acetyl-N-hydroxyamino)propen-3-yl]-4-(p-bromophenylthioethoxy)-3-methoxyphenyl]-2-(3,4,5-trimethoxyphenyl)tetrahydrofuran 4-[5-[trans-1-(N-Hydroxy-N-propanoylamino)propen-3-yl]-4-(p-chlorophenylthioethoxy)-3-methoxyphenyl]-2-(3,4,5-trimethoxyphenyl)tetrahydrofuran 4-[5-[trans-1-(N-Butanoyl-N-hydroxyamino)propen-3-yl]-4-(3,4-dichlorophenylthioethoxy)-3-methoxyphenyl]-2-(3,4,5-trimethoxyphenyl)tetrahydrofuran 4-[5-[trans-1-(N-Hydroxy-N-cyclohexanecarbonylamino)propen-3-yl]-4-(p-fluorophenylthioethoxy)-3-methoxyphenyl]-2-(3,4,5-trimethoxyphenyl)tetrahydrofuran 4-[5-[trans-1-(N-Hydroxy-N-phenoxybenzoylamino)propen-3-yl]-4-(2,3,5,6-tetrafluorophenylthioethoxy)-3-methoxyphenyl]-2-(3,4,5-trimethoxyphenyl)tetrahydrofuran 4-[5-[trans-1-(N-Hydroxy-N-methoxybenzoylamino)propen-3-yl]-4-(2-bromophenylthioethoxy)-3-methoxyphenyl]-2-(3,4,5-trimethoxyphenyl)tetrahydrofuran 4-[5-[trans-1-(N-Hydroxy-N-hydroxybenzoylamino)propen-3-yl]-4-(p-chlorophenylthioethoxy)-3-methoxyphenyl]-2-(3,4,5-trimethoxyphenyl)tetrahydrofuran Double Bonded Ureas: Both Cis and Trans Isomers at the Tetrahydrofuran Ring.

4-[5-[trans-1-(N'-Hydroxy-N'-methylureidyl)propen-3-yl]-4-(p-chlorophenylthioethoxy)-3-methoxyphenyl]-2-(3,4,5-trimethoxyphenyl)tetrahydrofuran 4-[5-[trans-1-(N'-Ethyl-N'-hydroxyureidyl)propen-3-yl]-4-(p-chlorophenylthioethoxy)-3-methoxyphenyl]-2-(3,4,5-trimethoxyphenyl)tetrahydrofuran 4-[5-[trans-1-(N'-Hydroxy-N'-propylureidyl)propen-3-yl]-4-(p-chlorophenylthioethoxy)-3-methoxyphenyl]-2-(3,4,5-trimethoxyphenyl)tetrahydrofuran 4-[5-[trans-1-(N'-n-Butyl-N'-hydroxyureidyl)propen-3-yl]-4-(p-chlorophenylthioethoxy)-3-methoxyphenyl]-2-(3,4,5-trimethoxyphenyl)tetrahydrofuran 4-[5-[trans-1-(N'-Hydroxy-N'-i-propylureidyl)propen-3-yl]-4-(p-chlorophenylthioethoxy)-3-methoxyphenyl]-2-(3,4,5-trimethoxyphenyl)tetrahydrofuran 4-[5-[trans-1-(N'-tert-Butyl-N'-hydroxyureidyl)propen-3-yl]-4-(p-chlorophenylthioethoxy)-3-methoxyphenyl]-2-(3,4,5-trimethoxyphenyl)tetrahydrofuran 4-[5-[trans-1-(N'-Benzyl-N'-hydroxyureidyl)propen-3-yl]-4-(p-chlorophenylthioethoxy)-3-methoxyphenyl]-2-(3,4,5-trimethoxyphenyl)tetrahydrofuran 4-[5-[trans-1-(N'-Cyclopropyl-N'-hydroxyureidyl)propen-3-yl]-4-(p-chlorophenylthioethoxy)-3-methoxyphenyl]-2-(3,4,5-trimethoxyphenyl)tetrahydrofuran 4-[5-[trans-1-(N'-Allyl-N'-hydroxyureidyl)propen-3-yl]-4-(p-chlorophenylthioethoxy)-3-methoxyphenyl]-2-(3,4,5-trimethoxyphenyl)tetrahydrofuran 4-[5-[trans-1-(N'-Hydroxy-N'-hydroxyethylureidyl)propen-3-yl]-4-(p-chlorophenylthioethoxy)-3-methoxyphenyl]-2-(3,4,5-trimethoxyphenyl)tetrahydrofuran Formula III Cis and Trans Isomers of the Following Compounds:

2-(3-Methoxy-4-p-chlorophenylthioethoxy-5-N-methylaminophenyl)-5-(3,4,5-trimethoxyphenyl)-tetrahydrofuran 2-(3-Methoxy-4-p-chlorophenylthioethoxy-5-N-ethylaminophenyl)-5-(3,4,5-trimethoxyphenyl)-tetrahydrofuran 2-(3-Methoxy-4-p-chlorophenylthioethoxy-5-N,N-dipropylaminophenyl)-5-(3,4,5-trimethoxyphenyl)-tetrahydrofuran 2-(3-Methoxy-4-p-bromophenylthioethoxy-5-N,N-dipropylaminophenyl)-5-(3,4,5-trimethoxyphenyl)-tetrahydrofuran 2-(3-Methoxy-4-3,4-dichlorophenylthioethoxy-5-N,N-dipropylaminophenyl)-5-(3,4,5-trimethoxyphenyl)-tetrahydrofuran 2-(3-Methoxy-4-p-fluorophenylthioethoxy-5-N,N-dipropylaminophenyl)-5-(3,4,5-trimethoxyphenyl)-tetrahydrofuran 2-[3-Methoxy-4-(2,3,5,6-tetrafluorophenylthioethoxy)-5-N,N-dipropylaminophenyl]-5-(3,4,5-trimethoxyphenyl)-tetrahydrofuran 2-[3-Methoxy-4-(2-bromophenylthioethoxy)-5-N,N-dipropylaminophenyl]-5-(3,4,5-trimethoxyphenyl)-tetrahydrofuran 2-[3-Methoxy-4-p-chlorophenylthioethoxy-5-(1-pyrrolidinyl)phenyl]-5-(3,4,5-trimethoxyphenyl)-tetrahydrofuran 2-(3-Methoxy-4-p-chlorophenylthioethoxy-5-N,N-diethylaminophenyl)-5-(3,4,5-trimethoxyphenyl)-tetrahydrofuran 2-[3-Methoxy-4-p-chlorophenylthioethoxy-5-(4-morpholinyl)phenyl]-5-(3,4,5-trimethoxyphenyl)-tetrahydrofuran 2-(3-Methoxy-4-p-chlorophenylthioethoxy-5-N,N-dibutylaminophenyl)-5-(3,4,5-trimethoxyphenyl)-tetrahydrofuran B. Stereochemistry The 2,5-diaryl tetrahydrofurans, tetrahydrothiophenes, and pyrrolidines. 1,3-cyclopentanes, and the 2,4-diaryl tetrahydrofurans, tetrahydrothiophenes, and pyrrolidines disclosed herein exhibit a number of stereochemical configurations. Carbon atoms 2 and 5 (or 2 and 4, in the compounds of Formula II) in the center ring are chiral, and thus the center ring exists at a minimum as a diastereomeric pair. Each diastereomer exists as a set of enantiomers. Therefore, based on the chiral $C_2$ and $C_5$ (or $C_2$ and $C_4$, in Formula II) atoms alone, the compound is a mixture of four enantiomers.

If nonhydrogen substituents are located on carbon atoms 3 and 4 in the center ring, (or carbon atoms 3 and 5, in Formula II compounds) then the $C_3$ and $C_4$ atoms are also chiral, and can also exist as a diastereomeric pair, that is also a mixture of four enantiomers.

The R groups in the active compounds described herein can likewise include chiral carbons, and thus, optically active centers.

It is sometimes found that one or more enantiomers of a biologically active compound is more active, and perhaps less toxic, than other enantiomers of the same compound. Such enantiomerically enriched compounds are often preferred for pharmaceutical administration to humans. For example, it has been discovered that trans-2,5-diaryl tetrahydrothiophene and trans-2,5-diaryl tetrahydrofuran are often more active PAF receptor antagonists than their cis counterparts.

One of ordinary skill in the art can easily synthesize and separate the enantiomers of the disclosed compounds using chiral reagents and known procedures, and can evaluate the biological activity of the isolated enantiomer using methods disclosed herein or otherwise known. Through the use of chiral NMR shift reagents, polarimetry, or chiral HPLC, the optical enrichment of the compound can be determined.

Classical methods of resolution include a variety of physical and chemical techniques. Often the simplest and most efficient technique is repeated recrystallization. Recrystallization can be performed at any stage in the preparation of the compound, or the final enantiomeric product. If successful, this simple approach represents a method of choice.

When recrystallization fails to provide material of acceptable optical purity, other methods can be evaluated. If the compound is basic, one can use chiral acids that form diastereomeric derivatives that may possess significantly different solubility properties. Nonlimiting examples of chiral acids include malic acid, mandelic acid, dibenzoyl tartaric acid, 3-bromocamphor-8-sulfonic acid, 10-camphorsulfonic acid, and di-p-toluoyltartaric acid. Similarly, acylation of a free hydroxyl group with a chiral acid also results in the formation of diastereomeric derivatives whose physical properties may differ sufficiently to permit separation.

Enantiomerically pure or enriched compounds can be obtained by passing the racemic mixture through a chromatographic column that has been designed for chiral separations, including cyclodextrin bonded columns marketed by Rainin Corporation.

A variety of chemical reagents and experimental procedures have been developed in recent years to produce enantiomerically pure or enriched products. For example, individual 2S,5S or 2R,5R enantiomers of 2,5-diaryl tetrahydrofurans can be prepared by the method described by Corey et al, (Corey, E. J. et al., *Tetrahedron Letters* 29, 2899 (1988)).

C. Syntheses of Active Compounds

The 2,5-diaryl tetrahydrofurans and tetrahydrothiophenes disclosed herein can be prepared in a variety of ways known to those skilled in the art, including by methods disclosed in or obvious in view of methods disclosed in U.S. Pat. Nos. 4,539,332, 4,757,084, 4,996,203 and 5,001,123, and European Patent Application Nos. 90306234.7, 90306235.4, and 89202593.3.

1,3-Diaryl cyclopentanes can be prepared using the procedure of Graham, et al, (1,3-Diaryl Cyclopentanes: A New Class of Potent PAF Receptor Antagonists. 197th ACS National Meeting, Dallas, Tex., Apr. 9–14, 1989, Division of Medicinal Chemistry, poster no. 25 (abstract)), or by other known methods.

2,5-Diaryl pyrrolidines can be prepared by methods known to those skilled in the art, including that described by Boekvall, et al. (*J. Org. Chem.* 55, 826 (1990)).

2,4-Diaryl tetrahydrofurans and tetrahydrothiophenes and 2,4-diaryl pyrrolidines can also be prepared by adaptations of methods described herein, or by other known methods.

A general procedure for preparing a hydroxyurea is:

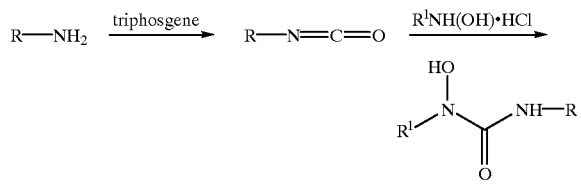

wherein R is a 2,5-diaryl tetrahydrothiophene, tetrahydrofuran, or pyrrolidine; 1,3-diaryl cyclopentane; or 2,4-diaryl tetrahydrothiophene, tetrahydrofuran or pyrrolidine; with or without a linking moiety, and R' is a moiety as defined in detail above.

General procedures for preparing reverse hydroxyureas are:

1.

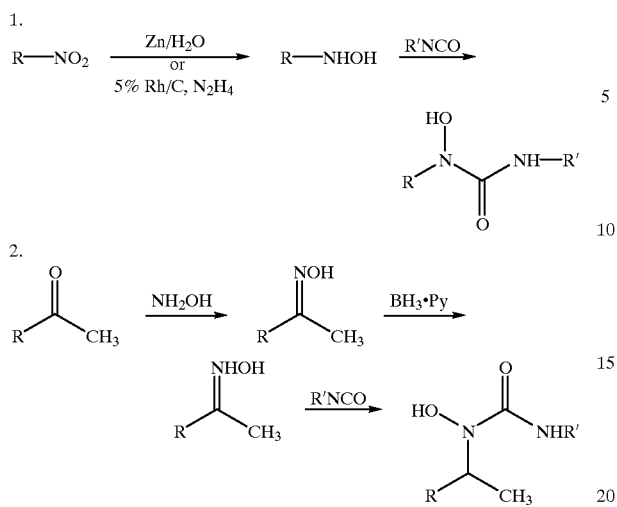

2.

A general procedure for preparing a hydroxamic acid is:

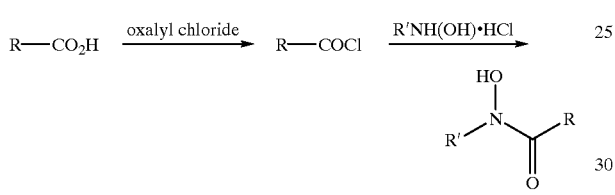

A general procedure for preparing a reverse hydroxamic acid is:

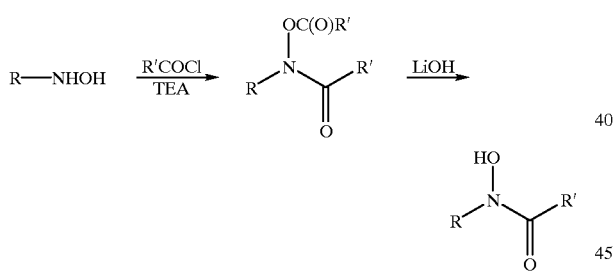

A general procedure for preparing amidohydroxyurea moieties is:

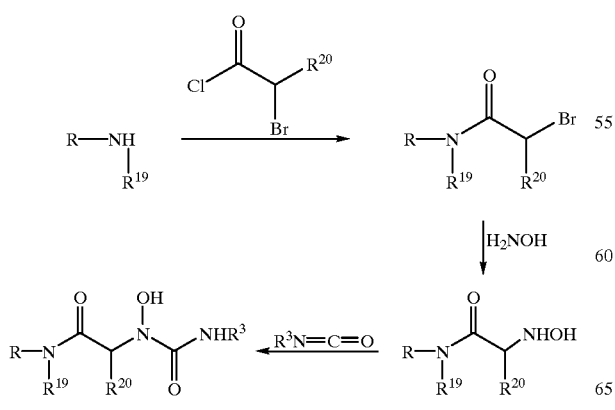

Oxalkanes and thioalkanes can be prepared as described by Crawley, et al. *J. Med. Chem.*, 35, 2600–2609 (1992), and illustrated below, by conversion of the desired moiety into a Grignard reagent or lithium salt, followed by reaction with the appropriate cyclic ketone.

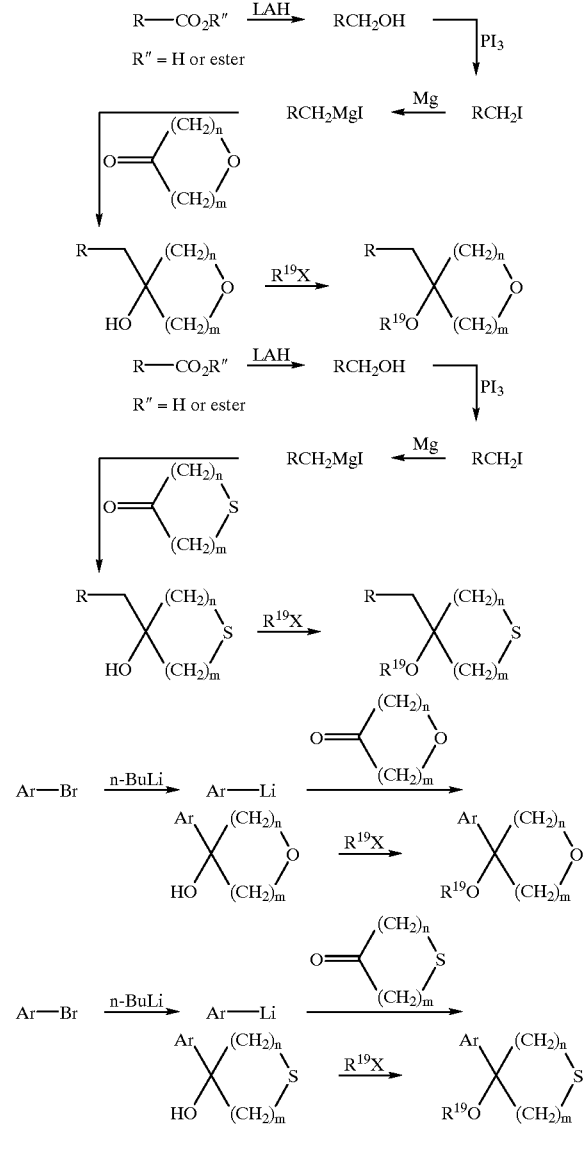

Quinolylmethoxy moieties can be prepared as described by Musser, et al., *J. Med. Chem.*, 35, 2501–2524 (1992), and references cited therein, as illustrated below.

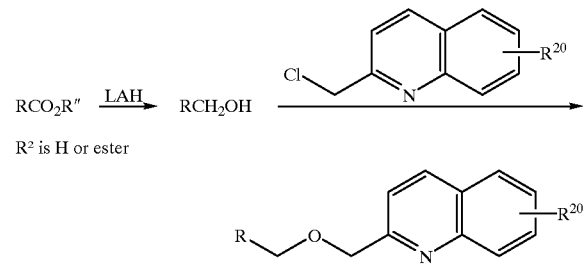

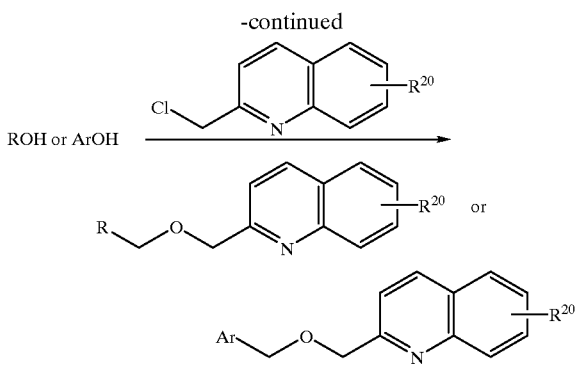

A method for the preparation of trans-2-[5-(N'-methyl-N'-hydroxyureidylmethyl)-3-methoxy-4-p-chlorophenylthioethoxyphenyl]-5-(3,4,5-trimethoxyphenyl) tetrahydrofuran is described in detail in the working example below. This example is merely illustrative, and not intended to limit the scope of the invention.

EXAMPLE 1

Figure 1B:
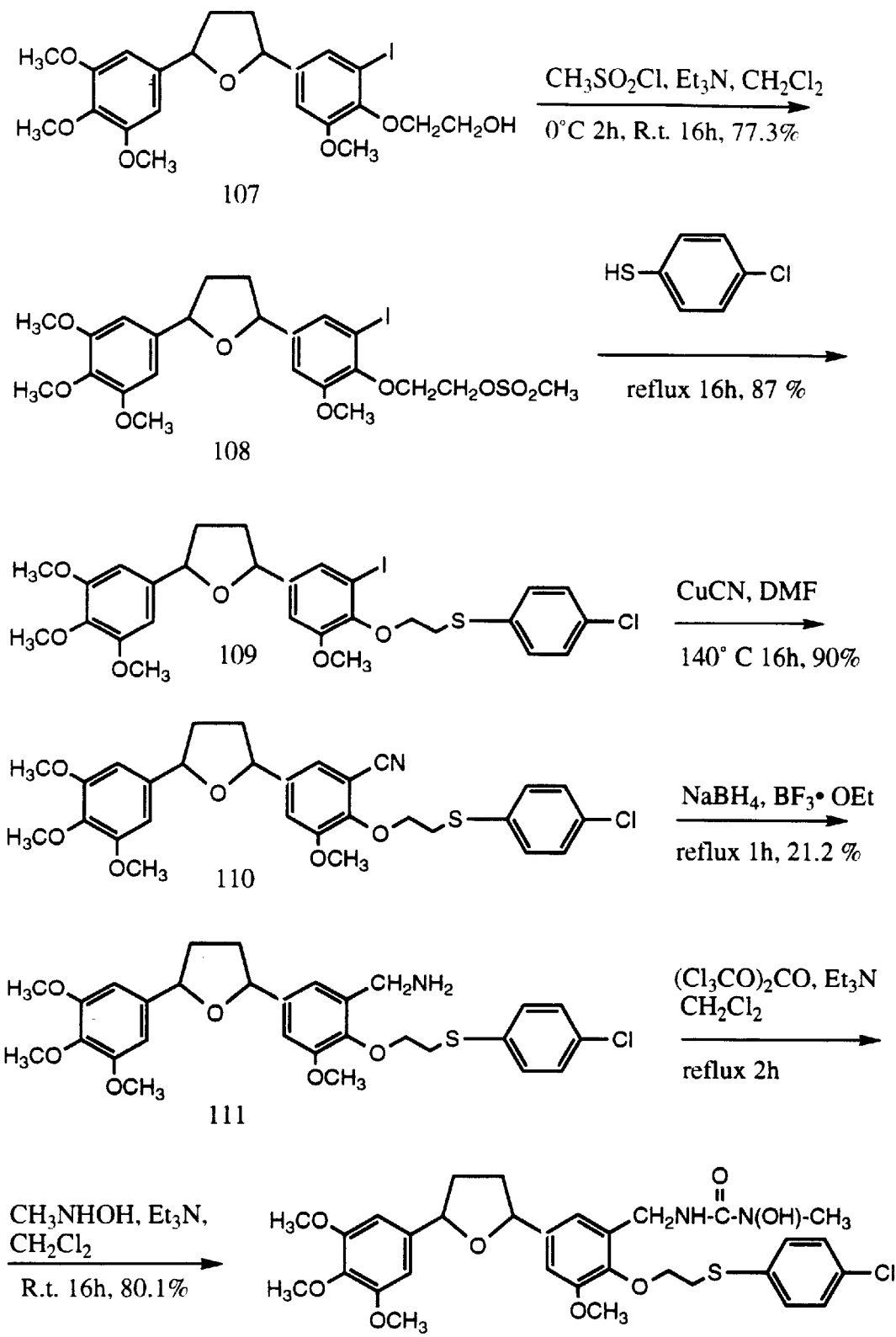

Preparation of trans-2-[5-(N'-methyl-N'-hydroxyureidylmethyl)-3-methoxy-4-p-chlorophenylthioethoxyphenyl]-5-(3,4,5-trimethoxyphenyl)tetrahydrofuran(29, FIGS. 1a and 1b)

3-(N,N-Dimethylamino)-1-(3,4,5-trimethoxyphenyl)-1-propanone (compound 101, FIG. 1). 3,4,5-Trimethoxyacetophenone (50 g, 237.8 mmole), paraformaldehyde (9.75 g, 304.7 mmole), dimethylamine hydrochloride (26.42 g, 324.0 mmole) and 5 mL conc. HCl were dissolved in 200 mL absolute ethanol and refluxed for 10 hours. Additional dimethylamine hydrochloride (13.21 g, 162.0 mmole) and paraformaldehyde (9.75 g, 304.7 mmole) were added and the solution returned to reflux. After 54 hours (total reaction time), 80 mL of 10% HCl and 500 mL of water were added and the solution was extracted with ethyl ether. The acidic aqueous layer was adjusted to pH 10 with 10% NaOH. The basic solution was extracted with ethyl acetate, dried over $MgSO_4$, filtered and evaporated in vacuo to provide 57.5 g of a yellow oil (92%). $^1$H NMR ($CDCl_3$): 2.30 (s, 6H); 2,74 (t, 2H); 3.11 (t, 3H); 3.91 (s, 9H); 7.23 (s, 1H); 7.32 (s, 1H).

3-(N,N,N-Trimethylamino)-1-(3,4,5-trimethoxyphenyl)-1-propanone iodide (compound 102, FIG. 1). 3-(N,N-Dimethylamino)-1-(3,4,5-trimethoxyphenyl)-1-propanone (57 g, 213.5 mmole) was dissolved in 200 mL of anhydrous diethyl ether. To this solution was added methyl iodide (57.6 g, 405.7 mmole). A white precipitate formed immediately, and the reaction mixture was stirred at room temperature for an additional 2 hours. This product was isolated by suction filtration (83.8 g, 96%).

3,4,5-Trimethoxyphenylvinylketone (compound 103, FIG. 1). 3-(N,N,N-Trimethylamino)-1-(3,4,5-trimethylphenyl)-1-propanone iodide (50 g, 120 mmole) was dissolved in $H_2O$ (500 mL) and ethyl acetate (500 mL) was added. The mixture was vigorously stirred at reflux for 3 hours. The reaction mixture was cooled and the layers were separated. To the aqueous phase was added ethyl acetate (400 mL). This was brought to reflux for 1.5 hours. The reaction mixture was cooled and separated. The combined organic layers were washed with saturated NaCl solution, dried over $Na_2SO_4$, filtered and concentrated in vacuo to an oil which was purified by flash column chromatography using 3:1 hexane/ethyl acetate as solvent (14.7 g, 54%). $^1$H NMR ($CDCl_3$): 3.92 (s, 9H); 5.92 (d, 1H); 6.44 (d, 1H); 7.12 (m, 1H); 7.22 (s, 2H).

3-Methoxy-4-hydoxyethoxy-5-iodobenzaldehyde (compound 104, FIG. 1). 5-Iodovanillin (25 g, 90 mmol) in DMF (100 mL) was added to potassium carbonate (18.6 g, 135 mmol). The mixture was heated at 40° C. for 16 hours. The reaction mixture was allowed to cool to room temperature and quenched with water (500 mL) and extracted with ethyl acetate. The organic layer was washed with water and saturated NaCl solution, and dried over $MgSO_4$, filtered and evaporated in vacuo to an oil, and then purified by column chromatography (silica, 2:1 hexane/ethyl acetate), to provide the product (16.6 g 57%). $^1$H NMR ($CDCl_3$): 2.70 (t, 1H); 3.92 (t, 2H); 3.92 (s, 3H); 3.94 (s, 3H); 4.29 (t, 2H); 7.44 (s, 1H); 7.87 (s, 1H); 9.85 (s, 1H).

1-(3-Methoxy-4-hydroxyethoxy-5-iodophenyl)-4-(3,4,5-trimethoxyphenyl)-1,4-butanedione (compound 105, FIG. 1). 3,4,5-Trimethoxyphenylvinylketone (4.8 g. 21.6 mmol). 3-methoxy-4-hydroxyethoxy-5-iodobenzaldehyde (5.7 g, 17.8 mmol), and 3-benzyl-5-(2-hydroxyethyl)-4-methylthiazolium chloride (1.9 g, 7.0 mmol) were stirred in trimethylamine (20 mL) at 60° C. for 16 hours. The reaction mixture was then acidified with 10% HCl, and extracted with dichloromethane. The organic layer was dried over $MgSO_4$, filtered and evaporated in vacuo. The product was purified in column chromatography (silica, 1:1 hexane/ethyl acetate) as a solid (9.7 g, 51%). $^1$H NMR ($CDCl_3$): 3.41 (m, 4H); 3.90 (m, 2H); 3.92 (s, 3H); 3.93 (s, 9H); 4.26 (t, 2H); 7.29 (s, 2H); 7.57 (d, 1H); 8.08 (d, 1H).

1-(3-Methoxy-4-hydroxyethoxy-5-iodophenyl)-4-(3,4,5-trimethoxyphenyl)-1,4-butanediol (compound 106, FIG. 1). 1-(3-Methoxy-4-hydroxyethoxy-5-iodophenyl)-4-( 3,4,5-trimethoxyphenyl)-1,4-butanedione (11.6 g, 21.3 mmol), was added to 120 mL tetrahydrofuran and 240 mL methanol. To this solution was added dropwise sodium borohydride (1.45 g, 38.4 mmol), in 60 mL water. The reaction mixture was stirred at room temperature for 2.5 hours, and then cooled, quenched with water, and the aqueous layer extracted with ethyl acetate. The organic layer was dried over $MgSO_4$, filtered and evaporated in vacuo to provide the product (11.8 g, 98.8%). $^1$H NMR ($CDCl_3$): 1.84 (m, 4H); 3.84 (m, 2H); 3.86 (s, 3H); 3.87 (s, 9H); 4.15 (t, 2H); 4.68 (m, 2H); 6.57 (s, 2H); 6.91 (s, 1H); 7.32 (s, 1H).

trans-2-(3-Methoxy-4-hydroxyethoxy-5-iodophenyl)-5-(3,4,5-trimethoxyphenyl)tetrahydrofuran (compound 107, FIG. 1). To 1-(3-methoxy-4-hydroxyethoxy-5-iodophenyl)-4-(3,4,5-trimethoxyphenyl)-1,4-butanediol (11.8 g, 21.5 mmol) in chloroform (100 mL) at 0° C. was added dropwise trifluoroacetic acid (9.82 g, 86.1 mmol) in chloroform (100 mL) over 30 minutes. The solution was stirred at 0° C. for 2 hours and then at room temperature for 1 hour. The reaction mixture was quenched with 1N NaOH and chloroform (100 mL) was added. The organic layer was washed with 1N NaOH solution, water and saturated NaCl solution, and then dried over $MgSO_4$, filtered and evaporated in vacuo to an oil which was a cis and trans mixture. The trans isomer was isolated by column chromatography (silica, 1:1 hexane/ethyl acetate) (4.7 g, 41.4%) as the faster eluting isomer. $^1$H NMR ($CDCl_3$): 1.99 (m, 2H); 2.47 (m, 2H): 3.83 (t, 2H); 3.84 (s, 3H); 3.87 (s, 3H); 3.89 (s, 6H); 4.16 (t, 2H); 5.18 (m, 2H); 6.62 (s, 2H); 6.96 (d, 1H); 7.39 (d, 1H).

trans-2-(3-Methoxy-4-methylsulfoxyethoxy-5-iodophenyl)-5-(3,4,5-trimethoxyphenyl)tetrahydrofuran (compound 108, FIG. 1). To the solution of trans-2-(3- methoxy-4-hydroxyethoxy-5-iodophenyl)-5-(3,4,5-trimethoxyphenyl)tetrahydrofuran (4.7 g, 8.87 mmol) in dichloromethane (50 mL) at 0° C. was added methylsulfonyl chloride (3.05 g, 26.6 mmole) and trimethylamine (2.69 g, 26.60 mmol). The reaction mixture was stirred at 0° C. for 2 hours and room temperature overnight. The solvent was evaporated in vacuo and the residue purified by column chromatography (silica, 1:1 hexane/ethyl acetate) (4.17 g, 77.3%). $^1$H NMR (CDCl$_3$): 1.98 (m, 2H); 2.45 (m, 2H); 3.15 (s, 3H); 3.84 (s, 3H); 3.88 (s, 9H); 4.26 (t, 2H); 4.61 (t, 2H); 5.17 (m, 2H); 6.62 (s, 2H); 6.96 (d, 1H); 7.38 (d, 1H).

trans-2-(3-Methoxy-4-p-chlorophenylthioethoxy-5-iodophenyl)-5-(3,4,5-trimethoxyphenyl)tetrahydrofuran (compound 109, FIG. 1). trans-2-(3-Methoxy-4-methylsulfoxyethoxy-5-iodophenyl)-5-(3,4,5-trimethoxyphenyl)tetrahydrofuran (2.5 g, 4.11 mmol) was dissolved in 50 mL ethanol. To this solution was added 4-chlorothiophenol (1.19 g, 8.22 mmol) and trimethylamine (0.831 g, 8.22 mmol). The reaction mixture was refluxed for 16 hours and then the solvent was removed in vacuo. The residue was purified by column chromatography (silica, 3:1 hexane/ethyl acetate)(2.35 g, 87%). $^1$H NMR (CDCl$_3$): 1.97 (m, 2H); 2.45 (m, 2H); 3.35 (t, 2H); 3.82 (s, 3H); 3.84 (s, 3H), 3.88 (s, 6H); 4.11 (t, 2H); 5.17 (m, 2H), 6.61 (s, 2H); 6.92 (s, 1H); 7.26 (d, 2H); 7.33 (d, 2H); 7.35 (s, 1H).

trans-2-(3-Methoxy-4-p-chlorophenylthioethoxy-5-cyanophenyl)-5-(3,4,5-trimethoxyphenyl)tetrahydrofuran (compound 110, FIG. 1). trans-2-(3-Methoxy-4-p-chlorophenylthioethoxy-5-iodophenyl)-5-(3,4,5-trimethoxyphenyl)tetrahydrofuran (2.35 g, 3.58 mmole) and CuCN (0.358 g, 4.30 mmole) in DMF (20 mL) were heated at 140° C. for 16 hours. The reaction mixture was cooled and quenched with water and extracted with ethyl acetate. The organic layer was washed with water and saturated NaCl solution, dried over MgSO$_4$, filtered and evaporated in vacuo to oil which was purified by column chromatography (silica, 2:1 hexane/ethyl acetate) (1.79 g, 90.0%). $^1$H NMR (CDCl$_3$): 1.99 (m, 2H); 2.47 (m, 2H); 3.32 (t, 2H); 3.85 (s, 6H), 3.89 (s, 6H); 4.27 (t, 2H); 5.17 (m, 2H); 6.61 (s, 2H); 7.16 (s, 2H); 7.28 (d, 2H); 7.32 (d, 2H).

trans-2-(3-Methoxy-4-p-chlorophenylthioethoxy-5-aminomethylphenyl)-5-(3,4,5-trimethoxyphenyl)tetrahydrofuran (compound 111, FIG. 1). To trans-2-(3-methoxy-4-p-chlorophenylthioethoxy-5-cyanophenyl)-5-(3,4,5-trimethoxyphenyl tetrahydrofuran (300 mg, 0.5405 mmol) in THF (10 mL) was added sodium borohydride (36.8 mg, 0.9729 mmol) and boron trifluoride etherate (191.8 mg. 1.3512 mmol) dropwise. The reaction mixture was refluxed for 1 hour, cooled, and then treated with a few drops of 10% HCl. The reaction mixture was poured into 10% K$_2$CO$_3$ and extracted with ethyl acetate. The organic layer was washed with water and saturated NaCl solution, dried over MgSO$_4$, filtered and evaporated in vacuo to an oil which was purified by column chromatography (silica, 93:7 CH$_2$Cl$_2$/MeOH) 64 mg, 21.2%). $^1$H NMR (CDCl$_3$): 1.99 (m, 2H); 2.46 (m, 2H); 3.28 (t, 2H); 3.84 (s, 6H); 3.88 (s, 6H); 4.26 (t, 2H); 5.19 (m, 2H); 6.71 (s, 2H); 6.90 (s, 2H); 7.25 (d, 2H); 7.32 (d, 2H).

trans-2-[5-(N'-Methyl-N'-hydroxyureidylmethyl)-3-methoxy-4-p-chlorophenylthioethoxypenyl]-5-(3,4,5-trimethoxyphenyl)tetrahydrofuran (29, FIG. 1). trans-2-(3-methoxy-4-p-chlorophenylthioethoxy-5-aminomethylphenyl)-5-(3,4,5-trimethoxyphenyl) tetrahydrofuran (54 mg, 0.0966 mmol) was dissolved in 4 mL dry dichloromethane. To this solution was added triphosgene (9.46 mg, 0.0319 mmol) and trimethylamine (9.77 mg, 0.0966 mmol). The reaction mixture was refluxed for 2 hours and then cooled to room temperature. To this solution was then added trimethylamine (35.2 mg, 0.3478 mmol) and methylhydroxyamine hydrochloride (24.2 mg. 0.2898 mmol). The reaction mixture was stirred at room temperature overnight, and then quenched with water and extracted with dichloromethane. The organic layer was washed with water and saturated NaCl solution, dried over MgSO$_4$, filtered and evaporated in vacuo. The product was purified by column chromatography (silica, ethyl acetate) (49 mg, 80.1%). $^1$H NMR (CDCl$_3$): 1.97 (m, 2H); 2.43 (m, 2H); 3.08 (s, 3H); 3.27 (t, 2H); 3.82 (s, 3H); 3.83 (s, 3H); 3.87 (s, 6H); 4.15 (t, 2H); 4.39 (d, 2H); 5.17 (m, 2H); 6.41 (t, 1H); 6.51 (s, 2H); 6.78 (broad s, 1 H); 6.90 (s, 2H); 7.24 (d, 2H); 7.31 (d, 2H).

II. Pharmaceutical Compositions

Humans, equine, canine, bovine and other animals, and in particular, mammals, suffering from inflammatory diseases, and in particular, disorders mediated by PAF or products of 5-lipoxygenase can be treated by administering to the patient an effective amount of one or more of the above-identified compounds or a pharmaceutically acceptable derivative or salt thereof in a pharmaceutically acceptable carrier or diluent to reduce formation of oxygen radicals. The active materials can be administered by any appropriate route, for example, orally, parenterally, intravenously, intradermally, subcutaneously, or topically, in liquid, cream, gel or solid form.

As used herein, the term pharmaceutically acceptable salts or complexes refers to salts or complexes that retain the desired biological activity of the above-identified compounds and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. The compounds can also be administered as pharmaceutically acceptable quaternary salts known by those skilled in the art, which specifically include the quaternary ammonium salt of the formula —NR+Z—, wherein R is alkyl or benzyl, and Z is a counterion, including chloride, bromide, iodide, -O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate.

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01–3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The compound is conveniently administered in any suitable unit dosage form, including but not limited to one containing 1 to 3000 mg, preferably 5 to 500 mg of active ingredient per unit dosage form. A oral dosage of 25–250 mg is usually convenient.

The active ingredient should be administered to achieve peak plasma concentrations of the active compound of about 0.01–30 mM, preferably about 0.1–10 mM. This may be achieved, for example, by the intravenous injection of a solution or formulation of the active ingredient, optionally in saline, or an aqueous medium or administered as a bolus of the active ingredient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid. Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable derivatives or salts thereof can also be mixed with other active materials that do not impair the desired action, or with materials that supplement the desired action, such as antibiotics, antifungals, other antiinflammatories, or antiviral compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation (CA) and Scios Nova (Baltimore, Md.). Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated. leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

III. Biological Activity

A wide variety of biological assays have been used to evaluate the ability of a compound to act as a PAF receptor antagonist, including the ability of the compound to bind to PAF receptors, and the effect of the compound on various PAF mediated pathways. Any of these known assays can be used to evaluate the ability of the compounds disclosed herein to act as PAF receptor antagonists.

For example, PAF is known to induce hemoconcentration and increased permeability of microcirculation leading to a decrease in plasma volume. PAF mediated acute circulatory collapse can be used as the basis of an assay to evaluate the ability of a compound to act as a PAF antagonist, by analyzing the effect of the compound on PAF induced decreased plasma volume in an animal model such as mouse. Endotoxemia causes the release of chemical mediators including eicosanoids, PAF, and tumor necrosis factor (TNF) that stimulate a variety of physiologic responses including fever, hypotension, leukocytosis, and disturbances in glucose and lipid metabolism. Endotoxemia can result in severe shock and death. Endotoxin-induced mouse mortality is a useful animal model to evaluate the pharmacological effect of compounds on endotoxic shock.

Two other common assays used to evaluate the ability of a compound to act as a PAF receptor antagonist are platelet aggregation in vitro and hypotension in rats (Shen, et al., "The Chemical and Biological Properties of PAF Agonists, Antagonists, and Biosynthetic Inhibitors", *Platelet-Activating Factor and Related Lipid Mediators*, F. Snyder, Ed. Plenum Press, New York, N.Y. 153 (1987)). A wide variety of biological assays have also been used to evaluate the ability of a compound to inhibit the enzyme 5-lipoxygenase. For example, a cytosol 5-lipoxygenase of rat basophilic leukemia cells (RBL) has been widely utilized in studies on leukotriene biosynthesis. Compounds that inhibit 5-lipoxygenase decrease the levels of leukotrienes. Another biological assay used to evaluate the ability of a compound to inhibit the enzyme 5-lipoxygenase is based on the classic pharmacological model of inflammation induced by the topical application of arachidonic acid to the mouse ear. On application, arachidonic acid is converted by 5-lipoxygenase to various leukotrienes (and other mediators), which induce changes in blood flow, erythema, and increase vasodilation and vasopermeability. The resulting edema is measured by comparing the thickness of the treated ear to a control ear. Agents that inhibit 5-lipoxygenase reduce the edematous response, by lowering the amounts of biochemical mediators formed from arachidonic acid.

EXAMPLE 2

Ability of Compound to Bind to PAF Receptors
a) Preparation of Human Platelet Membranes Human platelet membranes were prepared from platelet concentrates obtained from the American Red Cross Blood Services (Dedham, Mass.). After several washes with platelet wash solution (150 mM NaCl, 10 mM Tris, and 2 mM EDTA, pH 7.5), the platelet pellets were resuspended in 5 mM $MgCl_2$, 10 mM Tris, and 2 mM EDTA at pH 7.0. The cells were then quickly frozen with liquid nitrogen and thawed slowly at room temperature. The freezing and thawing procedure was repeated at least three times. For further fractionation of membrane fragments, the lysed membrane suspension was layered over the top of a discontinuous sucrose density gradient of 0.25, 1.03, and 1.5 M sucrose prepared in 10 mM $MgCl_2$, 10 mM Tris and 2 mM EDTA, pH 7.0, and centrifuged at 63,500×g for 2 hr. The membrane fractions banding between 0.25 and 1.03 M (membrane A) and between 1.03 and 1.5 M (membrane B) were collected separately. The protein concentration of the membrane preparations was determined by Lowry's method with bovine serum albumin (BSA) as the standard. The membranes were then separated into smaller fractions (4 ml each) and stored at −80° C. and thawed before use.

b) [$^3$H]PAF Binding Inhibition

The ability of [$^3$H]PAF to bind to specific receptors on human platelet membranes was evaluated at optimal conditions at pH 7.0 and in the presence of 10 mM $MgCl_2$. Membrane protein (100 μg) was added to a final 0.5 ml solution containing 0.15 pmol (0.3 nM concentration) of [$^3$H]PAF and a known amount of unlabeled PAF or PAF receptor antagonist in 10 mM $MgCl_2$, 10 mM Tris and 0.25% BSA at pH 7.0. After incubation for four hours at 0° C., the bound and unbound [$^3$H]PAF were separated through a Whatman GF/C glass fiber filter under vacuum. No degradation of filter bound [$^3$H]PAF has been detected under this assay condition. The nonspecific binding was defined as the total binding in the presence of excess unlabeled PAF (1 mM) where no further displacement was found with higher concentrations of either unlabeled PAF or PAF analogs or PAF receptor antagonists. The specific binding was defined as the difference between total binding and nonspecific binding.

To determine the relative potency of tested compounds, [$^3$H]PAF binding in the presence of inhibitors was normalized in terms of percent inhibition by assigning the total binding in the absence of inhibitors as 0% inhibition and the total binding in the presence of 1 mM unlabeled PAF as 100%. The percent inhibition by the compound can be calculated by the formula expressed below:

% inhibition=[(Total binding−total binding in the presence of compound)/nonspecific binding]×100%

The $IC_{50}$ was calculated as the concentration of the inhibitor necessary to obtain 50% inhibition of the specific [$^3$H]PAF binding and was calculated by a nonlinear regression computer software program. GraphPad Inplot, version 3.0 (GraphPad software, San Diego, Calif.). Tables 1 and 2 provide $IC_{50}$ values for a number of the disclosed compounds.

TABLE 1

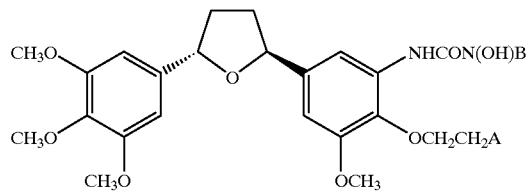

| | | | $IC_{50}$(nM) | |
| Compounds | A | B | PAF | 5-LO |
|---|---|---|---|---|
| 1 | S-Ph-p-Br* | $CH_2CH_2CH_2CH_3$ | 20.9 | 18.7 |
| 2 | $SO_2$-Ph-p-Br | $CH_2CH_2CH_2CH_3$ | 38.3 | |
| 3 | S-Ph-2-Br | $CH_2CH_2CH_2CH_3$ | 23.0 | 33.0 |
| 4 | $SO_2$-Ph-2-Br | $CH_2CH_2CH_2CH_3$ | 25.0 | 161.0 |
| 5 | S-Ph-3-Br | $CH_2CH_2CH_2CH_3$ | 16.0 | 43.3 |
| 6 | S-Ph-p-F | $CH_2CH_2CH_2CH_3$ | 45.0 | 63.8 |
| 7 | S-Ph-2,3,5,6-F | $CH_2CH_2CH_2CH_3$ | 2.2 | 118.4 |
| 8 | $SO_2$-Ph-2,3,5,6-F | $CH_2CH_2CH_2CH_3$ | 285.3 | 520.2 |
| 9 | O-Ph-2,3,5,6-F | $CH_2CH_2CH_2CH_3$ | 55.3 | 132.8 |
| 10 | S-Ph-p-Cl | $CH_2CH_2CH_2CH_3$ | 10.0 | 58.5 |

TABLE 1-continued

[Structure: 2,5-disubstituted tetrahydrofuran with 3,4,5-trimethoxyphenyl on one side and on the other side a phenyl bearing NHCON(OH)B, OCH₂CH₂A, and OCH₃ substituents]

| Compounds | A | B | IC$_{50}$(nM) PAF | IC$_{50}$(nM) 5-LO |
|---|---|---|---|---|
| 11 | S-Ph-3,4-Cl | CH$_2$CH$_2$CH$_2$CH$_3$ | 45.0 | 17.4 |
| 12 | S-Ph-p-OH | CH$_2$CH$_2$CH$_2$CH$_3$ | 5.53 | 180.0 |
| 13 | S-Ph-p-OCH$_3$ | CH$_2$CH$_2$CH$_2$CH$_3$ | 39.2 | 71.2 |
| 14 | S-Ph-p-CN | CH$_2$CH$_2$CH$_2$CH$_3$ | 62.6 | 62.3 |
| 15 | SCH$_3$ | CH$_2$CH$_2$CH$_2$CH$_3$ | 13.5 | 190.0 |
| 16 | OCH$_3$ | CH$_2$CH$_2$CH$_2$CH$_3$ | 195.2 | |
| 17 | 3-fluoro-5-(4-methoxytetrahydropyran-4-yl)phenoxy | CH$_2$CH$_2$CH$_2$CH$_3$ | 281.0 | 87.0 |
| 18 | 2-(quinolin-2-ylmethoxy)·HCl | CH$_2$CH$_2$CH$_2$CH$_3$ | | 390.6 |
| 19 | 3-fluoro-5-(4-methoxytetrahydropyran-4-yl)phenoxy | CH$_3$ | 321.2 | 719.0 |
| 20 | 3-fluoro-5-(4-methoxytetrahydropyran-4-yl)phenoxy | CH$_2$Ph | 622.7 | 900.9 |
| 21 | 3-fluoro-5-(4-methoxytetrahydropyran-4-yl)phenoxy | CH$_2$CH$_2$CH$_2$CH$_3$ | 321.8 | 366.3 |
| 22 | 3-(N-phenylcarbamoyl)pyridin-yl-methoxy | CH$_2$CH$_2$CH$_2$CH$_3$ | 16.3 | 479.0 |

TABLE 1-continued

[Structure: CH3O, CH3O, CH3O-substituted phenyl—tetrahydrofuran—phenyl with NHCON(OH)B, OCH2CH2A, OCH3 substituents]

| Compounds | A | B | IC$_{50}$(nM) PAF | 5-LO |
|---|---|---|---|---|
| 23 | N(Ph)CO-pyridinium-propyl, I⁻ | CH$_2$CH$_2$CH$_2$CH$_3$ | 197.4 | |
| 24 | N(Ph)CO-pyridyl | Ph-p-Cl | 84.2 | |
| 25 | N(Ph)CO-pyridinium-propyl, I⁻ | Ph-p-Cl | 6285 | 670.0 |
| 26 | CH$_3$ | Ph-p-Cl | 217.6 | 533.0 |
| 27 | S-Ph-p-OH | Ph-p-Cl | 26.9 | 3000 |
| 28 | SCH$_3$ | Ph-p-Cl | 317.7 | 3000 |

*Ph = phenyl

TABLE 2

[Structure: CH3O, CH3O, CH3O-substituted phenyl—tetrahydrofuran—phenyl with B, OCH2CH2A, OCH3 substituents]

| Compounds | A | B | IC$_{50}$(nM) PAF | 5-LO |
|---|---|---|---|---|
| 29 | S-Ph-p-Cl | CH$_2$NHCON(OH)CH$_3$ | 7.60 | 22.2 |
| 30 | S-Ph-p-Cl | CH$_2$N(CH$_2$CH$_2$CH$_3$)CON(OH)CH$_3$ | 7.40 | |
| 31 | S-Ph-p-Cl | CH$_2$N(OH)CONH$_2$ | 33.2 | 34.2 |
| 32 | S-Ph-p-Cl | CH$_2$N(OH)CONHCH$_3$ | 7.06 | 185.0 |
| 33 | S-Ph-p-Cl | NHCOCH$_2$N(OH)CONH$_2$ | 47.5 | 318.0 |
| 34 | S-Ph-p-Cl | NHCOCH$_2$N(OH)CONHCH$_3$ | 3318.8 | |
| 35 | O-Ph-p-F | ≡—CH$_2$N(OH)CONH$_2$ | 73.9 | 828.2 |
| 36 | S-Ph-p-Cl | ≡—CH$_2$N(OH)CONH$_2$ | 11.3 | |

EXAMPLE 3

Effect of Compound on PAF-induced Hemoconcentration a) Animals

Female CD-1 mice, weighing 16–20 grams, were obtained from Charles River Laboratory (Wilmington, Mass.). Tap water and rodent laboratory chow (5001, Purina Mills, St. Louis. Mo.) were provided ad libitum. The mice were housed for an average of four days prior to use.

b) Hematocrit Measurement

PAF (1-O-alkyl-2-acetyl-sn-glyceryl-3-phosphorylcholine, Sigma Chemical Co.) was dissolved in 0.25% bovine serum albumin (BSA) in 0.9% NaCl solution. Except for dose-response studies, 10 μg (10 ml/kg) of PAF solution was injected into the tail vein. All test compounds were dissolved in 0.5 DMSO saline solution and intravenously injected at 3 mg/kg body weight 15 minutes prior to PAF challenge. Thirty to fifty μL brood was collected by cutting the tail end into a heparinized micro-hematocrit tube (O.D. 1.50 mm) 15 minutes after PAF administration. Table 2 provides the mouse hematocrit response to varying concentration of PAF at 15 minutes after injection of PAF. Tables 3 and 4 provide the effect of various test compounds on PAF-induced mouse hemoconcentration; the reference compound MK287 is trans-2-(3,4,5-trimethoxy)-5-(3-methoxy-4-oxyallyl-(2-hydroxyethylsulfonyl))-tetrahydrofuran. (Sahoo. et al., Bioorganic Medicinal Chem. Letters, (1991), 1, 327.)

EXAMPLE 4

Effect of 2.5-Diaryl Tetrahydrothiophenes and Tetrahydrofurans on Arachidonic Acid-induced Mouse Ear Edema a) Animals The animals were obtained and treated as in Example 3 above.

b) Edema measurement

Arachidonic acid was applied to both ears of mice in 0.025 ml of freshly prepared vehicle (acetone:pyridine:water) (97:2:1 v/v/v) and dried under a Sun-Lite Hitensity bulb. Except for dose-response studies, 0.5 mg of arachidonic acid was used for all applications. All test compounds were dissolved in 0.5% DMSO saline solution and intravenously injected at 3 mg/kg body weight 15 minutes prior to arachidonic acid treatment. Animals were sacrificed by cervical dislocation at 1 hour after topical application of arachidonic acid. A 7 mm-diameter disc of tissue was removed from each ear by means of a metal punch. Edema was measured by the average wet weight of the both ear tissues.

Tables 3 and 4 provides the effect of various test compounds on arachidonic acid induced mouse ear edema

TABLE 3

| | | | InH (%)* | |
|---|---|---|---|---|
| Compounds | A | B | PAF-Htc | AA-Ed |
| 1 | S-Ph-p-Br | CH$_2$CH$_2$CH$_2$CH$_3$ | −10.5 | −2.7 |
| 2 | SO$_2$-PH-p-Br | CH$_2$CH$_2$CH$_2$CH$_3$ | 29.3 | 34.5 |
| 3 | S-Ph-2-Br | CH$_2$CH$_2$CH$_2$CH$_3$ | 34.2 | 26.3 |
| 4 | SO$_2$-Ph-2-Br | CH$_2$CH$_2$CH$_2$CH$_3$ | 60.4 | −9.1 |
| 5 | S-Ph-3-Br | CH$_2$CH$_2$CH$_2$CH$_3$ | 28.2 | 40.2 |
| 6 | S-Ph-p-F | CH$_2$CH$_2$CH$_2$CH$_3$ | 33.6 | |
| 7 | S-Ph-2,3,5,6-F | CH$_2$CH$_2$CH$_2$CH$_3$ | 58.8 | 30.4 |
| 8 | SO$_2$-Ph-2,3,5,6-F | CH$_2$CH$_2$CH$_2$CH$_3$ | 50.4 | 11.9 |
| 9 | O-Ph-2,3,5,6-F | CH$_2$CH$_2$CH$_2$CH$_3$ | 59.1 | 29.2 |
| 10 | S-Ph-p-Cl | CH$_2$CH$_2$CH$_2$CH$_3$ | 25.3 | 39.2 |
| 11 | S-Ph-3,4-Cl | CH$_2$CH$_2$CH$_2$CH$_3$ | 26.1 | 26.3 |
| 12 | S-Ph-p-OH | CH$_2$CH$_2$CH$_2$CH$_3$ | 33.5 | 49.9 |
| 13 | S-Ph-p-OCH$_3$ | CH$_2$CH$_2$CH$_2$CH$_3$ | 23.6 | 2.7 |
| 14 | S-Ph-p-CN | CH$_2$CH$_2$CH$_2$CH$_3$ | −12.4 | 46.5 |
| 15 | SCH$_3$ | CH$_2$CH$_2$CH$_2$CH$_3$ | 11.1 | 41.1 |
| 16 | OCH$_3$ | CH$_2$CH$_2$CH$_2$CH$_3$ | 11.2 | |

TABLE 3-continued

| | | | InH (%)* | |
|---|---|---|---|---|
| Compounds | A | B | PAF-Htc | AA-Ed |
| 17 | (2-quinolinyl-OCH$_2$-) | CH$_2$CH$_2$CH$_2$CH$_3$ | 26.1 | 57.0 |
| 19 | (3,5-disubst. aryl, F) | CH$_3$ | 49.6 | 47.8 |
| 20 | (3,5-disubst. aryl, F) | CH$_2$Ph | 63.1 | 49.9 |
| 21 | (3,5-disubst. aryl, F) | CH$_2$CH$_2$CH$_2$CH$_3$ | 70.4 | 57.0 |
| 26 | CH$_3$ | Ph-p-Cl | | 23.7 |

*All test compounds were given intravenously at 3 mg/kg 15 minutes before PAF (10 μg/kg, intravenously) or AA (0.5 mg/ear) in mice.

TABLE 4

| | | | InH (%)* | |
|---|---|---|---|---|
| Compounds | A | B | PAF-Htc | AA-Ed |
| 29 | S-Ph-p-Cl | CH$_2$NHCON(OH)CH$_3$ | 55.7 | 45.6 |
| 31 | S-Ph-p-Cl | CH$_2$N(OH)CONH$_2$ | 57.9 | 23.6 |
| 32 | S-Ph-p-Cl | CH$_2$N(OH)CONHCH$_3$ | 41.1 | 10.3 |
| 33 | S-Ph-p-Cl | NHCOCH$_2$N(OH)CONH$_2$ | 2.1 | 51.1 |

TABLE 4-continued

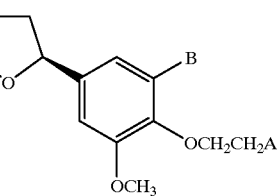

| Compounds | A | B | InH (%)* PAF-Htc | AA-Ed |
|---|---|---|---|---|
| 34 | S-Ph-p-Cl | NHCOCH$_2$N(OH)CONHCH$_3$ | −9.8 | 31.0 |
| 35 | O-Ph-p-F | ≡—CH$_2$N(OH)CONH$_2$ | 99.5 | 24.5 |

*All test compounds were given intravenously at 3 mg/kg 15 minutes before PAF (10 μg/kg, intravenously) or AA (0.5 mg/ear) in mice.
Ph = phenyl

EXAMPLE 5

Effect of 2,5-Diaryl Tetrahydrothiophenes and Tetrahydrofurans on Endotoxin-induced Mouse Mortality a) Animals The mice are obtained and treated as in Example 3 above.

b) Mortality Measurement

Endotoxin (E. coli serotype 0127:B8, lipopolysaccharide, Sigma Chemical Co. (St. Louis, Mo.) are freshly dissolved in 0.9% NaCl solution. Except for dose-response studies, endotoxin at 50 mg/kg is injected into the tail vein. All test compounds are dissolved in 0.5% DMSO saline solution and intravenously injected at 3 mg/kg body weight 15 minutes prior to PAF challenge. Death occurs typically within 12–36 hours. Mortality is recorded 48 hours after endotoxin challenge, as death rarely occurs after 48 hours.

EXAMPLE 6

Effect of Compounds on Cytosol 5-Lipoxygenase of Rat Basophile Leukemia Cells a) Enzyme Preparation Washed rat RBL cells (4×108) are suspended in 20 ml of 50 M potassium phosphate buffer at pH 7.4 containing 10% ethylene glycol/1 mM EDTA (Buffer A). The cell suspension is sonicated at 20 KHz for 30 seconds, and the sonicate is centrifuged at 10,000×g for 10 minutes, followed by further centrifugation at 105,000×g for 1 hr. The supernatant solution (cytosol fraction) containing 5-lipoxygenase is stored at −70° C. Protein concentration is determined according to the procedure of Bradford (Bradford Dye Reagent) with bovine serum albumin as a standard.

b) Enzyme Assay

For routine assay of 5-LO the mixture contains 50 mM potassium phosphate buffer at pH 7.4, 2 mM CaCl$_2$, 2 mM ATP, 25 M arachidonic acid (0.1 Ci) and enzyme (50–100 mg of protein) in a final volume of 200 L. The reaction is carried out at 24° C. for 3 minutes. The mixture is extracted with 0.2 ml of an ice-cold mixture of ethyl ether:methanol: 0.2 M citric acid (30:4:1). The extract is subjected to thin-layer chromatography at −10° C. in a solvent system of petroleum ether:ethyl ether:acetic acid (15:85:0.1). The silica gel zones corresponding to authentic arachidonic acid and its metabolites are scraped into scintillation vials for counting. The enzyme activity is expressed in terms of the amount of arachidonic acid oxygenated for 3 minutes.

Modifications and variations of the present invention relating to compounds that reduce the formation of oxygen radicals during an inflammatory or immune response will be obvious to those skilled in the art from the foregoing detailed description of the invention. Such modifications and variations are intended to come within the scope of the appended claims.

We claim:

1. A method for the treatment of disorder mediated by platelet activating factor or products of 5-lipoxygenase in an animal, comprising adminstering an effective amount of trans-2-[5-N'-methyl-N'-hydroxyureidylmethyl)-3-methoxy-4-p-chlorophenylthioethoxphenyl]-5-(3,4,5-trimethoxphenyl)tetrahydrofuran or its pharmaceutically acceptable salt.

2. The method of claim 1, wherein the animal is a mammal.

3. The method of claim 1, wherein the animal is a human.

4. The method of claim 1, wherein the mammal is equine.

5. The method of claim 1, wherein the mammal is canine.

6. The method of claim 1, wherein the mammal is bovine.

7. The method of claim 1, wherein the disorder is psoriasis.

8. The method of claim 1, wherein the disorder is inflammatory bowel disease.

9. The method of claim 1, wherein the disorders are respiratory including, but not limited to, asthma, adult respiratory distress disorder (ARDS), and rhinitis.

10. The method of claim 1, wherein the disorder is ophthalmic inflammatory disorder.

* * * * *